United States Patent [19]
Barbachyn et al.

[11] Patent Number: 6,093,736
[45] Date of Patent: Jul. 25, 2000

[54] ISOXAZOLINE DERIVATIVES USEFUL AS ANTIMICROBIALS

[75] Inventors: Michael Robert Barbachyn; Richard Charles Thomas; Gary J. Cleek, all of Kalamazoo, Mich.

[73] Assignee: Pharmacia & Upjohn Company

[21] Appl. No.: 09/386,647

[22] Filed: Aug. 31, 1999

Related U.S. Application Data

[62] Division of application No. 08/999,753, Aug. 15, 1997
[60] Provisional application No. 60/024,287, Aug. 21, 1996.
[51] Int. Cl.[7] ............ A61K 31/44; A61K 31/42; C07D 413/00; C07D 261/02
[52] U.S. Cl. ............ 514/340; 514/378; 546/272.1; 548/240
[58] Field of Search ................... 514/340, 378; 546/272.1; 548/240

[56] References Cited

U.S. PATENT DOCUMENTS

| | | | |
|---|---|---|---|
| 3,769,295 | 10/1973 | Hoyle et al. | 260/307 |
| 4,283,403 | 8/1981 | Davenport | 424/263 |
| 5,710,159 | 1/1998 | Voss et al. | 514/275 |

FOREIGN PATENT DOCUMENTS

| | | | |
|---|---|---|---|
| 2725763 | of 0000 | Denmark . | |
| 352 781 | 1/1990 | European Pat. Off. ...... | C07D 263/20 |
| 0 693 491 | 1/1996 | European Pat. Off. ...... | C07D 413/04 |
| 0 694 543 | 1/1996 | European Pat. Off. ...... | C07D 413/04 |
| 94 13649 | 6/1994 | WIPO ................. | C07D 263/20 |
| 95/14680 A1 | 6/1995 | WIPO ................. | C02D 261/04 |

OTHER PUBLICATIONS

S. S. Ghabrial, et al., Acta Chemica Scandinavica, B 41, pp. 426–434 (1987).

*Primary Examiner*—Mukund J. Shah
*Assistant Examiner*—Bruck Kifle
*Attorney, Agent, or Firm*—Lucy X. Yang

[57] ABSTRACT

The present invention provides compounds of formula I

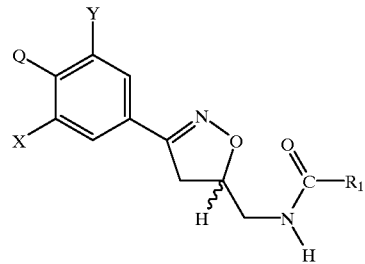

or a pharmaceutical acceptable salt thereof wherein Q, X, Y and $R_1$ are as defined in the claims which are antibacterial agents.

12 Claims, No Drawings

ISOXAZOLINE DERIVATIVES USEFUL AS ANTIMICROBIALS

CROSS-REFERENCE TO RELATED APPLICATION

This application is a divisional of U.S. patent application, Ser. No. 08/999,753, filed Aug. 15, 1997, which claims the benefit of the U.S. provisional application, Serial No. 60/024,287, filed Aug. 21, 1996, under 35 USC 119(e)(i).

FIELD OF THE INVENTION

The present invention relates to novel isoxazoline derivatives or pharmaceutically acceptable salts thereof which are useful as antibacterial agents.

BACKGROUND OF THE INVENTION

Antibacterial agents such as oxazolidinones are a class of known orally-active, synthetic antibacterial agents and there are numerous references in the art disclosing a variety of oxazolidinone derivatives. For example, U.S. Pat. Nos. 4,705,799 and 5,523,403 and European Patent Application 0,316,594 disclose substituted phenyl-2-oxazolidinones, including the sulfides, sulfoxides, sulfones, sulfonamides, nitriles, acetamides and a tropone ring. U.S. Pat. Nos. 4,948,801; 5,254,577 and 5,130,316, disclose arylbenzene oxazolidinyl compounds, wherein the aryl includes the (un)substituted phenyl and pyridyl groups. European Patent Applications 0,697,412; 0,694,544; 0,694,543 and 0,693,491 disclose 5 to 9-membered heteroaryl-oxazolidinones having one to three atoms selected from the group consisting of sulfur, nitrogen and oxygen.

This invention describes isoxazoline derivatives which are effective as antibacterial agents. The compounds of the invention are novel and distinct from all other oxazolidinones in that the usual oxazolidinone rings are replaced by an isoxazoline moiety. These compounds have antibacterial activity comparable to the corresponding oxazolidinones. They are effective against a number of human and veterinary pathogens, including gram-positive aerobic bacteria such as multiply-resistant staphylococci and streptococci, as well as anaerobic organisms such as bacteroides and clostridia species, and acid-fast organisms such as *Mycobacterium tuberculosis* and *Mycobacterium avium*.

INFORMATION DISCLOSURE

U.S. Pat. No. 4,283,403 disclosed 3-aryl-2-isoxazolines useful for the protection of plants from disease.

Danish Patent No. 2,725,763 disclosed substituted 2-isoxazolines which is fungicidal against phytophthora infestation on tomatoes. The compounds also show antibacterial activity.

U.S. Pat. No. 3,769,295 disclosed nitrofuryl derivatives of 5-substituted isoxazolines useful as antimicrobial agents.

WO 95/14680 A1 disclosed 3-aryl-2-isoxazolines which is useful in inhibiting $PDE_{IV}$, the treatment of inflammatory diseases and the treatment of AIDs, asthma, arthritis, etc.

S. S. Ghabrial, et al., Acta Chemical Scandinavica, B 41, pp. 426–434 (1987) discloses the synthesis of heteroaromatic compounds via the isoxazoline route.

SUMMARY OF THE INVENTION

The present invention provides new antibacterial compounds of the formula I

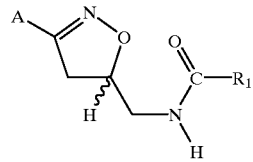

or a pharmaceutical acceptable salt thereof wherein:
$R_1$ is
  a) H,
  b) $C_{1-8}$ alkyl optionally substituted with one or more F, Cl, OH, $C_{1-4}$ alkoxy, or acyloxy,
  c) $C_{3-6}$ cycloalkyl, or
  d) $C_{1-8}$ alkoxy;
A is
  a)

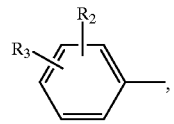

b)

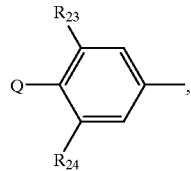

c)

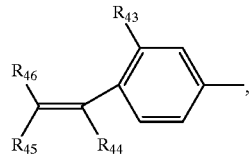

d) a 5-membered heteroaromatic moiety having one to three atoms selected from the group consisting of S, N, and O,
    wherein the 5-membered heteroaromatic moiety is bonded via a carbon atom,
    wherein the 5-membered heteroaromatic moiety can additionally have a fused-on benzene or naphthyl ring,
    wherein the heteroaromatic moiety is optionally substituted with one to three $R_{48}$,
  e) a 6-membered heteroaromatic moiety having at least one nitrogen atom,
    wherein the heteroaromatic moiety is bonded via c carbon atom,
    wherein the 6-membered heteroaromatic moiety can additionally have a fused-on benzene or naphthyl ring,
    wherein the heteroaromatic moiety is optionally substituted with one to three $R_{55}$,
  f) a β-carbolin-3-yl, or indolizinyl bonded via the 6-membered ring, optionally substituted with one to three $R_{55}$, g) 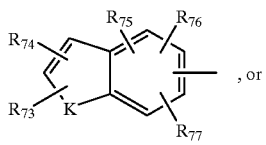, or h) 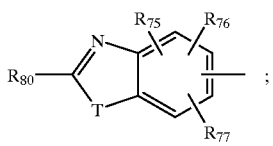;

wherein $R_2$ is
 a) H,
 b) F,
 c) Cl,
 d) Br,
 e) $C_{1-3}$ alkyl,
 f) $NO_2$, or
 g) $R_2$ and $R_3$ taken together are $-O-(CH_2)_n-O-$;
$R_3$ is
 a) $-S(=O)_iR_4$,
 b) $-S(=O)_2-N=S(O)_jR_5R_6$,
 c) $-SC(=O)R_7$,
 d) $-C(=O)R_8$,
 e) $-C(=O)R_9$,
 f) $-C(=O)NR_{10}R_{11}$,
 g) $-C(=NR_{12})R_8$,
 h) $-C(R_8)(R_{11})-OR_{13}$,
 i) $-C(R_9)(R_{11})-OR_{13}$,
 j) $-C(R_8R_{11})-OC(=O)R_{13}$,
 k) $-C(R_9R_{11})-OC(=O)R_{13}$,
 l) $-NR_{10}R_{11}$,
 m) $-N(R_{10})-C(=O)R_7$,
 n) $-N(R_{10})-S(=O)_iR_7$,
 o) $-C(OR_{14})(OR_{15})R_8$,
 p) $-C(R_8)(R_{16})-NR_{10}R_{11}$, or
 q) $C_{1-8}$ alkyl substituted with one or more $=O$ other than at alpha position, $-S(=O)_iR_{17}$, $-NR_{10}R_{11}$, $C_{2-5}$ alkenyl, or $C_{2-5}$ alkynyl;
$R_4$ is
 a) $C_{1-4}$ alkyl optionally substituted with one or more halos, OH, CN, $NR_{10}R_{11}$, or $-CO_2R_{13}$,
 b) $C_{2-4}$ alkenyl,
 c) $-NR_{16}R_{18}$,
 d) $-N_3$,
 e) $-NHC(=O)R_7$,
 f) $-NR_{20}C(=O)R_7$,
 g) $-N(R_{19})_2$,
 h) $-NR_{16}R_{19}$, or
 i) $-NR_{19}R_{20}$;
$R_5$ and $R_6$ at each occurrence are the same or different and are
 a) $C_{1-2}$ alkyl, or
 b) $R_5$ and $R_6$ taken together are $-(CH_2)_k-$;
$R_7$ is $C_{1-4}$ alkyl optionally substituted with one or more halos;

$R_8$ is
 a) H, or
 b) $C_{1-8}$ alkyl optionally substituted with one or more halos, or $C_{3-8}$ cycloalkyl;
$R_9$ is $C_{1-4}$ alkyl substituted with one or more
 a) $-S(=O)R_{17}$,
 b) $-OR_{13}$,
 c) $-OC(=R)R_{13}$,
 d) $-NR_{10}R_{11}$, or
 e) $C_{1-5}$ alkenyl optionally substituted with CHO;
$R_{10}$ and $R_{11}$ at each occurrence are the same or different and are
 a) H,
 b) $C_{1-4}$ alkyl, or
 c) $C_{3-8}$ cycloalkyl;
$R_{12}$ is
 a) $-NR_{10}R_{11}$,
 b) $-OR_{10}$; or
 c) $-NHC(=O)R_{10}$;
$R_{13}$ is
 a) H, or
 b) $C_{1-4}$ alkyl;
$R_{14}$ and $R_{15}$ at each occurrence are the same or different and are
 a) $C_{1-4}$ alkyl, or
 b) $R_{14}$ and $R_{15}$ taken together are $-(CH)_l-$;
$R_{16}$ is
 a) H,
 b) $C_{1-4}$ alkyl, or
 c) $C_{3-8}$ cycloalkyl;
$R_{17}$ is
 a) $C_{1-4}$ alkyl, or
 b) $C_{3-8}$ cycloalkyl;
$R_{18}$ is
 a) H,
 b) $C_{1-4}$ alkyl,
 c) $C_{2-4}$ alkenyl,
 d) $C_{3-4}$ cycloalkyl,
 e) $-OR_{13}$, or
 f) $-NR_{21}R_{22}$;
$R_{19}$ is
 a) Cl,
 b) Br, or
 c) I;
$R_{20}$ is a physiologically acceptable cation;
$R_{21}$ and $R_{22}$ at each occurrence are the same or different and are
 a) H,
 b) $C_{1-4}$ alkyl, or
 c) $-NR_{21}R_{22}$ taken together are $-(CH_2)_m-$;
where $R_{23}$ and $R_{24}$ at each occurrence are the same or different and are
 a) H,
 b) F,
 c) Cl,
 d) $C_{1-2}$ alkyl,
 e) CN,
 f) OH,
 g) $C_{1-2}$ alkoxy, h) nitro, or i) amino;

Q is a) 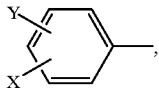

b) 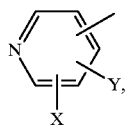

c) 

d) 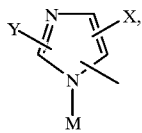

e) 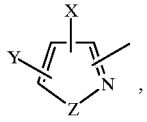

f) 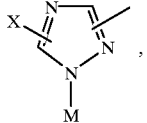

g) 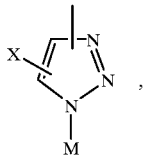

h) 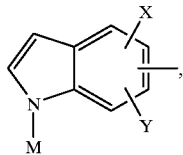

i) 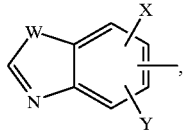

j) 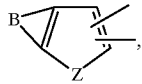

k) 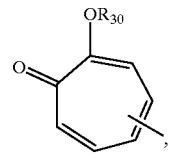

l) 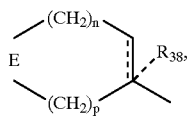

m) a diazinyl group optionally substituted with X and Y, n) a triazinyl group optionally substituted with X and Y, o) a quinolinyl group optionally substituted with X and Y, p) a quinoxalinyl group optionally substituted with X and Y, or q) a naphthyridinyl group optionally substituted with X and Y;

B is an unsaturated 4-atom linker having one nitrogen and three carbons;

M is
a) H,
b) $C_{1-8}$ alkyl,
c) $C_{3-8}$ cycloalkyl,
d) —$(CH_2)_m OR_{13}$, or
e) —$(CH_2)_n$—$NR_{21}R_{22}$;

Z is
a) O,
b) S, or
c) NM;

W is
a) CH,
b) N, or
c) S or O when Z is NM;

Y is
a) H,
b) F,
c) Cl,
d) Br,
e) $C_{1-3}$ alkyl, or
f) $NO_2$;

X is
a) H,
b) —CN,
c) $OR_{27}$,
d) halo,
e) $NO_2$,
f) tetrazoyl,
g) —SH,
h) —$S(=O)_i R_4$,
i) —$S(=O)_2$—$N=S(O)_j R_5 R_6$,
j) —$SC(=O)R_7$,
k) —$C(=O)R_{25}$,
l) —$C(=O)NR_{27}R_{28}$,
m) —$C(=NR_{29})R_{25}$,
n) —$C(R_{25})(R_{28})$—$OR_{13}$, o) —C(R$_{25}$)(R$_{28}$)—OC(=O)R$_{13}$,
p) —C(R$_{28}$)(OR$_{13}$)—(CH$_2$)$_n$—NR$_{27}$R$_{28}$,
q) —NR$_{27}$R$_{28}$,
r) —N(R$_{27}$)C(=O)R$_7$,
s) —N(R$_{27}$)—S(=O)$_i$R$_7$,
t) —C(OR$_{14}$)(OR$_{15}$)R$_{28}$,
u) —C(R$_{25}$)(R$_{16}$)—NR$_{27}$R$_{26}$, or
v) C$_{1-8}$ alkyl substituted with one or more halos, OH, =O other than at alpha position, —S(=O)$_i$R$_{17}$, —NR$_{27}$R$_{28}$, C$_{2-5}$ alkenyl, C$_{2-5}$ alkynyl, or C$_{3-8}$ cycloalkyl;

R$_4$, R$_5$, R$_6$, R$_7$, R$_{13}$, R$_{14}$, R$_{15}$, R$_{16}$, and R$_{17}$ are the same as defined above;

R$_{25}$ is
a) H,
b) C$_{1-8}$ alkyl optionally substituted with one or more halos, C$_{3-8}$ cycloalkyl, C$_{1-4}$ alkyl substituted with one or more of —S(=O)$_i$R$_{17}$, —OR$_{13}$, or OC(=O)R$_{13}$, NR$_{27}$R$_{28}$, or
c) C$_{2-5}$ alkenyl optionally substituted with CHO, or CO$_2$R$_{13}$;

R$_{26}$ is
a) R$_{28}$, or
b) NR$_{27}$N$_{28}$;

R$_{27}$ and R$_{28}$ at each occurrence are the same or different and are
a) H,
b) C$_{1-8}$ alkyl,
c) C$_{3-8}$ cycloalkyl,
d) —(CH$_2$)$_m$OR$_{13}$,
e) —(CH$_2$)$_n$—NR$_{21}$R$_{22}$, or
f) R$_{27}$ and R$_{28}$ taken together are —(CH$_2$)$_2$O(CH$_2$)$_2$—, —(CH$_2$)$_n$CH(COR$_7$)—, or —(CH$_2$)$_2$N(CH$_2$)$_2$(R$_7$);

R$_{29}$ is
a) —NR$_{27}$R$_{28}$,
b) —OR$_{27}$, or
c) —NHC(=O)R$_{28}$;

wherein R$_{30}$ is
a) H,
b) C$_{1-8}$ alkyl optionally substituted with one or more halos, or
c) C$_{1-8}$ alkyl optionally substituted with one or more OH, or C$_{1-6}$ alkoxy;

wherein E is
a) NR$_{39}$,
b) —S(=O)$_i$, or
c) O;

R$_{38}$ is
a) H,
b) C$_{1-6}$ alkyl,
c) —(CH$_2$)$_q$-aryl, or
d) halo;

R$_{39}$ is
a) H,
b) C$_{1-6}$ alkyl optionally substituted with one or more OH, halo, or —CN,
c) —(CH$_2$)$_q$-aryl,
d) —CO$_2$R$_{40}$,
e) —COR$_{41}$,
f) —C(=O)—(CH$_2$)$_q$—C(=O)R$_{40}$,
g) —S(=O)$_2$—C$_{1-6}$ alkyl,
h) —S(=O)$_2$—(CH$_2$)$_q$-aryl, or
i) —(C=O)$_j$-Het;

R$_{40}$ is
a) H,
b) C$_{1-6}$ alkyl optionally substituted with one or more OH, halo, or —CN,
c) —(CH$_2$)$_q$-aryl, or
d) —(CH$_2$)$_q$—OR$_{42}$;

R$_{41}$ is
a) C$_{1-6}$ alkyl optionally substituted with one or more OH, halo, or —CN,
b) —(CH$_2$)$_q$-aryl, or
c) —(CH$_2$)$_q$—OR$_{43}$;

R$_{42}$ is
a) H,
b) C$_{1-6}$ alkyl,
c) —(CH$_2$)$_q$-aryl, or
d) —C(=O)—C$_{1-6}$ alkyl;

aryl is
a) phenyl,
b) pyridyl, or
c) naphthyl, wherein sections a to c can be optionally substituted with one or more halo, —CN, OH, SH, C$_{1-6}$ alkyl, C$_{1-6}$ alkoxy, or C$_{1-6}$ alkylthio;

wherein R$_{43}$ is
a) H,
b) C$_{1-2}$ alkyl,
c) F, or
d) OH;

R$_{44}$ is
a) H,
b) CF$_3$,
c) C$_{1-3}$ alkyl optionally substituted with one or more halo,
d) phenyl optionally substituted with one or more halo,
e) R$_{44}$ and R$_{45}$ taken together are a 5-, 6-, or 7-membered ring of the formula,

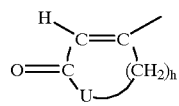

or
f) R$_{44}$ and R$_{45}$ taken together are —(CH$_2$)$_k$—, when R$_{46}$ is an electron-withdrawing group;

R$_{45}$ and R$_{46}$ at each occurrence are the same or different and are
a) an electron-withdrawing group,
b) H,
c) CF$_3$,
d) C$_{1-3}$ alkyl optionally substituted with one halo,
e) phenyl, provided at least one of R$_{45}$ or R$_{46}$ are an electron-withdrawing group, or
f) R$_{45}$ and R$_{46}$ taken together are a 5-, 6-, 7-membered ring of the formula

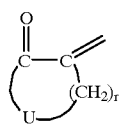

U is
  a) $CH_2$,
  b) O,
  c) S, or
  d) $NR_{47}$;
$R_{47}$ is
  a) H, or
  b) $C_{1-5}$ alkyl;
wherein $R_{48}$ is
  a) carboxyl,
  b) halo,
  c) —CN,
  d) mercapto,
  e) formyl,
  f) $CF_3$,
  g) —$NO_2$,
  h) $C_{1-6}$ alkoxy,
  i) $C_{1-6}$ alkoxycarbonyl,
  j) $C_{1-6}$ alkythio,
  k) $C_{1-6}$ acyl,
  l) —$NR_{49}R_{50}$,
  m) $C_{1-6}$ alkyl optionally substituted with OH, $C_{1-5}$ alkoxy, $C_{1-5}$ acyl, or —$NR_{49}R_{50}$,
  n) $C_{2-8}$ alkenylphenyl optionally substituted with one or two $R_{51}$,
  o) phenyl optionally substituted with one or two $R_{51}$,
  p) a 5-, or 6-membered (un)saturated heterocyclic moiety having one to three atoms selected from the group consisting of S, N, and O, optionally substituted with one or two $R_{51}$, or
  q)

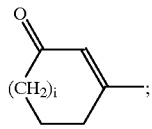

$R_{49}$ and $R_{50}$ at each occurrence are the same or different and are
  a) H,
  b) $C_{1-4}$ alkyl,
  c) $C_{5-6}$ cycloalkyl, or
  d) $R_{49}$ and $R_{50}$ taken together with the nitrogen atom is a 5-, 6-membered saturated heterocyclic moiety which optionally has a further hetero atom selected from the group consisting of S, N, and O, and can in turn be optionally substituted with, including on the further nitrogen atom, $C_{1-3}$ alkyl, or $C_{1-3}$ acyl;
$R_{51}$ is
  a) carboxyl,
  b) halo,
  c) —CN,
  d) mercapto,
  e) formyl,
  f) $CF_3$,
  g) —$NO_2$,
  h) $C_{1-6}$ alkoxy,
  i) $C_{1-6}$ alkoxycarbonyl,
  j) $C_{1-6}$ alkythio,
  k) $C_{1-6}$ acyl,
  l) $C_{1-6}$ alkyl optionally substituted with OH, $C_{1-5}$ alkoxy, $C_{1-5}$ acyl, or —$NR_{49}R_{50}$,
  m) phenyl,
  n) —C(=O)$NR_{52}R_{53}$,
  o) —$NR_{49}R_{50}$,
  p) —N($R_{52}$)(—$SO_2R_{54}$),
  q) —$SO_2$—$NR_{52}R_{53}$, or
  r) —S(=O)$_iR_{54}$;
$R_{52}$ and $R_{53}$ at each occurrence are the same or different and are
  a) H,
  b) $C_{1-6}$ alkyl, or
  c) phenyl;
$R_{54}$ is
  a) $C_{1-4}$ alkyl, or
  b) phenyl optionally substituted with $C_{1-4}$ alkyl;
wherein $R_{55}$ is
  a) carboxyl,
  b) halo,
  c) —CN,
  d) mercapto,
  e) formyl,
  f) $CF_3$,
  g) —$NO_2$,
  h) $C_{1-6}$ alkoxy,
  i) $C_{1-6}$ alkoxycarbonyl,
  j) $C_{1-6}$ alkythio,
  k) $C_{1-6}$ acyl,
  l) —$NR_{56}R_{57}$,
  m) $C_{1-6}$ alkyl optionally substituted with OH, $C_{1-5}$ alkoxy, $C_{1-5}$ acyl, or —$NR_{56}R_{57}$,
  n) $C_{2-8}$ alkenylphenyl optionally substituted with one or two $R_{58}$,
  o) phenyl optionally substituted with one or two $R_{58}$,
  p) a 5- or 6-membered (un)saturated heterocyclic moiety having one to three atoms selected from the group consisting of S, N, and O, optionally substituted with one or two $R_{58}$, or
  q)

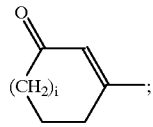

$R_{56}$ and $R_{57}$ at each occurrence are the same or different and are
  a) H,
  b) formyl,
  c) $C_{1-4}$ alkyl,
  d) $C_{1-4}$ acyl, e) phenyl, f) $C_{3-6}$ cycloalkyl, or g) $R_{56}$ and $R_{57}$ taken together with the nitrogen atom is a 5-, 6-membered saturated heterocyclic moiety which optionally has a further hetero atom selected from the group consisting of S, N, and O, and can in turn be optionally substituted with, including on the further nitrogen atom, phenyl, pyrimidyl, $C_{1-3}$ alkyl, or $C_{1-3}$ acyl;

$R_{58}$ is a) carboxyl, b) halo, c) —CN, d) mercapto, e) formyl, f) $CF_3$, g) —$NO_2$, h) $C_{1-6}$ alkoxy, i) $C_{1-6}$ alkoxycarbonyl, j) $C_{1-6}$ alkythio, k) $C_{1-6}$ acyl, l) phenyl, m) $C_{1-6}$ alkyl optionally substituted with OH, azido, $C_{1-5}$ alkoxy, $C_{1-5}$ acyl, —$NR_{65}R_{66}$, —$SR_{67}$, —O—$SO_2R_{68}$, or

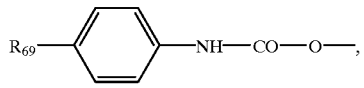

n) —C(=O)$NR_{59}R_{60}$, o) —$NR_{56}R_{57}$, p) —N($R_{59}$(—$SO_2R_{54}$), q) —$SO_2$—$NR_{59}R_{60}$, r) —S(=O)$_tR_{54}$, s) —CH=N—$R_{61}$, or t) —CH(OH)—$SO_3R_{64}$;

$R_{54}$ is the same as defined above;

$R_{59}$ and $R_{60}$ at each occurrence are the same or different and are a) H, b) $C_{1-6}$ alkyl, c) phenyl, or d) tolyl;

$R_{61}$ is a) OH, b) benzyloxy, c) —NH—C(=O)—$NH_2$, d) —NH—C(=S()—$NH_2$, or e) —NH—C(=NH)—$NR_{62}R_{63}$;

$R_{62}$ and $R_{63}$ at each occurrence are the same or different and are a) H, or b) $C_{1-4}$ alkyl optionally substituted with phenyl or pyridyl;

$R_{64}$ is a) H, or b) a sodium ion;

$R_{65}$ and $R_{66}$ at each occurrence are the same or different and are a) H, b) formyl, c) $C_{1-4}$ alkyl, d) $C_{1-4}$ acyl, e) phenyl, f) $C_{3-6}$ cycloalkyl, g) $R_{65}$ and $R_{66}$ taken together are a 5-, 6-membered saturated heterocyclic moiety having one to three atoms selected from the group consisting of S, N, and O, optionally substituted with, including on the nitrogen atom, phenyl, pyrimidyl, $C_{1-3}$ alkyl, or $C_{1-3}$ acyl, h) —P(O)($OR_{70}$)($OR_{71}$), or i) —$SO_2$—$R_{72}$;

$R_{67}$ is

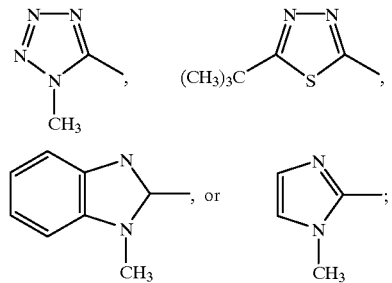

$R_{68}$ is $C_{1-3}$ alkyl;

$R_{69}$ is a) $C_{1-6}$ alkoxycarbonyl, or b) carboxyl;

$R_{70}$ and $R_{71}$ at each occurrence are the same or different and are a) H, or b) $C_{1-3}$ alkyl;

$R_{72}$ is a) methyl, b) phenyl, or c) tolyl;

wherein K is a) O, or b) S;

$R_{73}$, $R_{74}$, $R_{75}$, $R_{76}$, and $R_{77}$ at each occurrence are the same or different and are a) H, b) carboxyl, c) halo, d) —CN, e) mercapto, f) formyl, g) $CF_3$, h) —$NO_2$, i) $C_{1-6}$ alkoxy, j) $C_{1-6}$ alkoxycarbonyl, k) $C_{1-6}$ alkythio, l) $C_{1-6}$ acyl, m) —$NR_{78}R_{79}$, n) $C_{1-6}$ alkyl optionally substituted with OH, $C_{1-5}$ alkoxy, $C_{1-5}$ acyl, —$NR_{78}R_{79}$, —N(phenyl)($CH_2$—$CH_2$—

OH), —O—CH(CH$_3$)(OCH$_2$CH$_3$), or —O-phenyl-[para—NHC(=O)CH$_3$], o) C$_{2-8}$ alkenylphenyl optionally substituted with R$_{51}$, p) phenyl optionally substituted with R$_{51}$, or q) a 5-, or 6-membered (un)saturated heterocyclic moiety having one to three atoms selected from the group consisting of S, N, and O, optionally substituted with R$_{51}$;

R$_{51}$ is the same as defined above;

R$_{78}$ and R$_{79}$ at each occurrence are the same or different and are a) H, b) C$_{1-4}$ alkyl, c) phenyl, or d) R$_{78}$ and R$_{79}$ taken together with the nitrogen atom is a 5-, 6-membered saturated heterocyclic moiety which optionally has a further hetero atom selected from the group consisting of S, N, and O, and can in turn be optionally substituted with, including on the further nitrogen atom, C$_{1-3}$ alkyl, or C$_{1-3}$ acyl;

wherein T is a) O, b) S, or c) SO$_2$;

R$_{75}$, R$_{76}$, and R$_{77}$ are the same as defined above;

R$_{80}$ is a) H, b) formyl, c) carboxyl, d) C$_{1-6}$ alkoxycarbonyl, e) C$_{1-8}$ alkyl, f) C$_{2-8}$ alkenyl, wherein the substituents (e) and (f) can be optionally substituted with OH, halo, C$_{1-6}$ alkoxy, C$_{1-6}$ acyl, C$_{1-6}$ alkylthio or C$_{1-6}$ alkoxycarbonyl, or phenyl optionally substituted with halo, g) an aromatic moiety having 6 to 10 carbon atoms optionally substituted with carboxyl, halo, —CN, formyl, CF$_3$, —NO$_2$, C$_{1-6}$ alkyl, C$_{1-6}$ alkoxy, C$_{1-6}$ acyl, C$_{1-6}$ alkylthio, or C$_{1-6}$ alkoxycarbonyl, h) —NR$_{81}$R$_{82}$, i) —OR$_{90}$, j) —S(=O)$_f$—R$_{91}$, k) —SO$_2$—N(R$_{92}$)(R$_{93}$), or l) a radical of the following formulas:

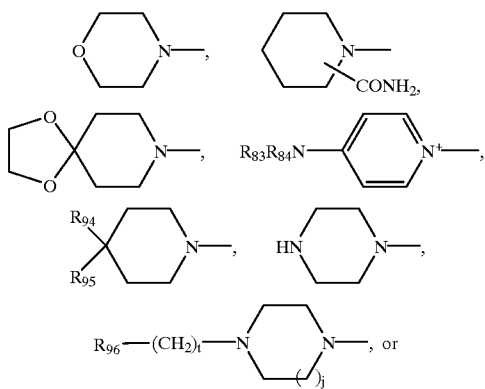

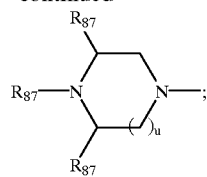

R$_{81}$ and R$_{82}$ at each occurrence are the same or different and are a) H, b) C$_{3-6}$ cycloalkyl, c) phenyl, d) C$_{1-6}$ acyl, e) C$_{1-8}$ alkyl optionally substituted with OH, C$_{1-6}$ alkoxy which can be substituted with OH, a 5-, or 6-membered aromatic heterocyclic moiety having one to three atoms selected from the group consisting of S, N, and O, phenyl optionally substituted with OH, CF$_3$, halo, —NO$_2$, C$_{1-4}$ alkoxy, —NR$_{83}$R$_{84}$, or f) 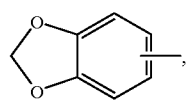

g) 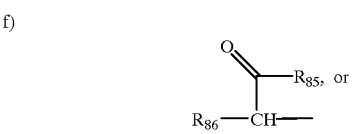

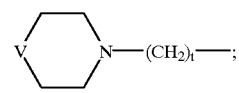

V is a) O, b) CH$_2$, or c) NR$_{87}$;

R$_{83}$ and R$_{84}$ at each occurrence are the same or different and are a) H, or b) C$_{1-4}$ alkyl;

R$_{85}$ is a) OH, b) C$_{1-4}$ alkoxy, or c) —NR$_{88}$R$_{89}$;

R$_{86}$ is a) H, or b) C$_{1-7}$ alkyl optionally substituted with indolyl, OH, mercaptyl, imidazoly, methylthio, amino, phenyl optionally substituted with OH, —C(=O)—NH$_2$, —CO$_2$H, or —C(=NH)—NH$_2$;

R$_{87}$ is a) H, b) phenyl, or c) C$_{1-6}$ alkyl optionally substituted by OH;

R$_{88}$ and R$_{89}$ at each occurrence are the same or different and are a) H, b) $C_{1-5}$ alkyl c) $C_{3-6}$ cycloalkyl, or d) phenyl;

$R_{90}$ is a) $C_{1-8}$ alkyl optionally substituted with $C_{1-6}$ alkoxy or $C_{1-6}$ hydroxy, $C_{3-6}$ cycloalkyl, a 6-membered aromatic optionally benzo-fused heterocyclic moiety having one to three nitrogen atoms, which can in turn be substituted with one or two —$NO_2$, $CF_3$, halo, —CN, OH, $C_{1-5}$ alkyl, $C_{1-5}$ alkoxy, or $C_{1-5}$ acyl;

b)

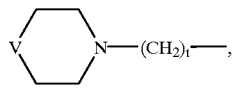

c) phenyl, or d) pyridyl;

$R_{91}$ is a) $C_{1-16}$ alkyl, b) $C_{2-16}$ alkenyl, wherein the substituents (a) and (b) can be optionally substituted with $C_{1-6}$ alkoxycarbonyl, or a 5-, 6-, 7-membered aromatic heterocyclic moiety having one to three atoms selected from the group consisting of S, N, and O, c) an aromatic moiety having 6 to 10 carbon atoms, or d) a 5-, 6-, 7-membered aromatic heterocyclic moiety having one to three atoms selected from the group consisting of S, N, and O, wherein the substituents (c) and (d) can be optionally substituted with carboxyl, halo, —CN, formyl, $CF_3$, —$NO_2$, $C_{1-6}$ alkyl, $C_{1-6}$ alkoxy, $C_{1-6}$ acyl, $C_{1-6}$ alkylthio, or $C_{1-6}$ alkoxycarbonyl;

$R_{92}$ and $R_{93}$ at each occurrence are the same or different and are a) H, b) phenyl, c) $C_{1-6}$ alkyl, or d) benzyl;

$R_{94}$ and $R_{95}$ at each occurrence are the same or different and are a) H, b) OH, c) $C_{1-6}$ alkyl optionally substituted with —$NR_{83}R_{84}$, or d) $R_{94}$ and $R_{95}$ taken together are =O;

$R_{96}$ is a) an aromatic moiety having 6 to 10 carbon atoms, b) a 5-, or 6-membered aromatic optionally benzo-fused heterocyclic moiety having one to three atoms selected from the group consisting of S, N, and O, wherein the substituents (a) and (b) which can in turn be substituted with one or three —$NO_2$, $CF_3$, halo, —CN, OH, phenyl, $C_{1-5}$ alkyl, $C_{1-5}$ alkoxy, or $C_{1-5}$ acyl, c) morpholinyl, d) OH, e) $C_{1-6}$ alkoxy, f) —$NR_{83}R_{84}$, g) —C(=O)—$R_{97}$, or h)

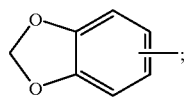

$R_{97}$ is a) morpholinyl, b) OH, or c) $C_{1-6}$ alkoxy;

h is 1, 2, or 3;

i is 0, 1, or 2;

j is 0 or 1;

k is 3, 4, or 5;

l is 2 or 3;

m is 4 or 5;

n is 0, 1, 2, 3, 4, or 5;

p is 0, 1, 2, 3, 4, or 5; with the proviso that n and p together are 1, 2, 3, 4, or 5;

q is 1, 2, 3, or 4;

r is 2, 3, or 4;

t is 0, 1, 2, 3, 4, 5, or 6;

u is 1 or 2; and with the following provisos:

a) A is not an unsubstituted pyridyl, thienyl, furyl, or pyrrolyl;

b) when $R_{48}$ is nitro, A is other than furyl;

c) when $R_{48}$ is chloro, A is other than thienyl; and d) when Q is

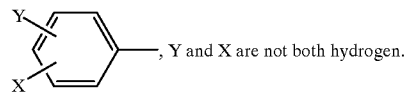, Y and X are not both hydrogen.

The compounds of the present invention have antibacterial activity. They are effective against a number of human and veterinary pathogens.

DETAILED DESCRIPTION OF THE INVENTION

For the purpose of the present invention, the carbon content of various hydrocarbon containing moieties is indicated by a prefix designating the minimum and maximum number of carbon atoms in the moiety, i.e., the prefix $C_{i-j}$ defines the number of carbon atoms present from the integer "i" to the integer "j", inclusive. Thus, $C_{1-4}$ alkyl refers to alkyl of 1–4 carbon atoms, inclusive, or methyl, ethyl, propyl, butyl and isomeric forms thereof.

The terms "$C_{1-2}$ alkyl", "$C_{1-3}$ alkyl", $C_{1-4}$ alkyl", $C_{1-5}$ alkyl", "$C_{1-6}$ alkyl", "$C_{1-8}$ alkyl", and "$C_{1-16}$ alkyl" refer to an alkyl group having one to two, one to three, one to four, one to five, one to six, one to eight, or one to sixteen carbon atoms respectively such as, for example, methyl, ethyl, propyl, butyl, pentyl, hexyl, heptyl, octyl, nonyl, decyl, undecyl, dodecyl, tridecyl, tetradecyl and their isomeric forms thereof.

The terms "$C_{2-4}$ alkenyl", "$C_{2-5}$ alkenyl", "$C_{2-8}$ alkenyl", "$C_{2-14}$ alkenyl" and "$C_{2-16}$ alkenyl" refer to at least one double bond alkenyl group having two to four, two to five, two to eight, two to fourteen, or two to sixteen carbon atoms, respectively such as, for example, ethenyl, propenyl, butenyl, pentenyl, pentdienyl, hexenyl, hexdienyl, heptenyl, heptdienyl, octenyl, octdienyl, octatrienyl, nonenyl, nonedienyl, nonatrienyl, undecenyl, undecdienyl, dodecenyl, tridecenyl, tetradecenyl and their isomeric forms thereof.

The terms "$C_{2-5}$ alkynyl", "$C_{2-8}$ alkynyl", and "$C_{2-10}$ alkynyl" refer to at least one triple bond alkynyl group having two to five, two to eight, or two to ten carbon atoms respectively such as, for example, ethynyl, propynyl, butynyl, pentynyl, pentdiynyl, hexynyl, hexdiynyl, heptynyl, heptdiynyl, octynyl, octdiynyl, octatriynyl, nonynyl, nonediynyl, nonatriynyl and their isomeric forms thereof.

The terms "$C_{3-4}$ cycloalkyl", "$C_{3-6}$ cycloalkyl", "$C_{5-6}$ cycloalkyl", and "$C_{3-8}$ cycloalkyl" refer to a cycloalkyl having three to four, three to six, five to six, or three to eight carbon atoms respectively such as, for example, cyclopropyl, cyclobutyl, cyclopentyl, cyclohexyl, cycloheptyl, cyclooctyl, and their isomeric forms thereof.

The terms "$C_{1-4}$ alkoxy", "$C_{1-6}$ alkoxy", and "$C_{1-8}$ alkoxy" refer to an alkyl group having one to four, one to six, or one to eight carbon atoms respectively attached to an oxygen atom such as, for example, methoxy, ethoxy, propyloxy, butyloxy, pentyloxy, hexyloxy, heptyloxy, or octyloxy and their isomeric forms thereof.

The terms "$C_{1-6}$ alkylamino", and "$C_{1-8}$ alkylamino" refer to an alkyl group having one to six, or one to eight carbon atoms respectively attached to an amino moiety such as, for example, methylamino, ethylamino, propylamino, butylamino, pentylamino, hexylamino, heptylamino, or octoylamino and their isomeric forms thereof.

The terms "$C_{1-6}$ dialkylamino", and "$C_{1-8}$ dialkylamino" refer to two alkyl groups having one to six, or one to eight carbon atoms respectively attached to an amino moiety such as, for example, dimethylamino, methylethylamino, diethylamino, dipropylamino, methypropylamino, ethylpropylamino, dibutylamino, dipentylamino, dihexylamino, methylhecylamino, diheptylamino, or dioctoylamino and their isomeric forms thereof.

The terms "$C_{1-3}$ acyl", "$C_{1-4}$ acyl", "$C_{1-5}$ acyl", "$C_{1-6}$ acyl", "$C_{1-8}$ acyl", and "$C_{2-8}$ acyl" refer to a carbonyl group having an alkyl group of one to three, one to four, one to five, one to six, one to eight, or two to eight carbon atoms.

The terms "$C_{1-4}$ alkoxycarbonyl", "$C_{1-6}$ alkoxycarbonyl", and "$C_{1-8}$ alkoxycarbonyl" refer to an ester group having an alkyl group of one to four, one to six, or one to eight carbon atoms.

The term "$C_{1-8}$ alkyl phenyl" refers to an alkyl group having one to eight carbon atoms and isomeric forms thereof which is substituted with at least one phenyl radical.

The term "$C_{2-8}$ alkenyl phenyl" refers to a at least one double bond alkenyl group having one to eight carbon atoms and isomeric forms thereof which is substituted with at least one phenyl radical.

The term "$C_{1-8}$ alkyl pyridyl" refers to an alkyl group having one to eight carbon atoms and isomeric forms thereof which is substituted with at least one pyridyl radical.

The term "$C_{1-8}$ hydroxyl" refers to an alkyl group having one to eight carbon atoms and isomeric forms thereof attached to a hydroxy group.

The term "$C_{1-8}$ alkylsulfonyl" refers to an alkyl group having one to eight carbon atoms and isomeric forms thereof attached to a $SO_2$ moiety.

The term "$C_{1-6}$ alkylthio" refers to an alkyl group having one to six carbon atoms and isomeric forms thereof attached to a sulfur atom.

The term "Het" refers to 5 to 10 membered saturated, unsaturated or aromatic heterocyclic rings containing one or more oxygen, nitrogen, and sulfur forming such groups as, for example, pyridine, thiophene, furan, pyrazoline, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 2-quinolyl, 3-quinolyl, 1-isoquinolyl, 3-isoquinolyl, 4-isoquinolyl, 2-quinazolinyl, 4-quinazolinyl, 2-quinoxalinyl, 1-phthalazinyl, 4-oxo-2-imidazolyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 4-oxo-2-oxazolyl, 5-oxazolyl, 4,5-dihydrooxazole, 1,2,3-oxathiole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-indolyl, 3-indolyl, 3-indazolyl, 2-benzoxazolyl, 2-benzothiazolyl, 2-benzimidazolyl, 2-benzofuranyl, 3-benzofuranyl, benzoisothiazole, benzisoxazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3,-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 1-pyrrolyl, 1-pyrazolyl, 1,2,3-triazol-1-yl, 1,2,4-triazol-1-yl, 1-tetrazolyl, 1-indolyl, 1-indazolyl, 2-isoindolyl, 7-oxo-2-isoindolyl, 1-purinyl, 3-isothiazolyl, 4-isothiazolyl and 5-isothiazolyl, 1,3,4,-oxadiazole, 4-oxo-2-thiazolinyl, or 5-methyl-1,3,4-thiadiazol-2-yl, thiazoledione, 1,2,3,4-thiatriazole, 1,2,4-dithiazolone. Each of these moieties may be substituted as appropriate.

The term "halo" refers to fluoro, chloro, bromo, or iodo.

The compounds of the present invention can be converted to their salts, where appropriate, according to conventional methods.

The term "pharmaceutically acceptable salts" refers to acid addition salts useful for administering the compounds of this invention and include hydrochloride, hydrobromide, hydroiodide, sulfate, phosphate, acetate, propionate, lactate, mesylate, maleate, malate, succinate, tartrate, citric acid, 2-hydroxyethyl sulfonate, fumarate and the like. These salts may be in hydrated form.

When Q is the structure of

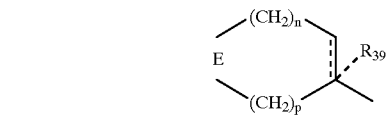

the dotted line in the heterocyclic ring means that this bond can be either single or double. In the case where the dotted line is a double bond, the $R_{39}$ group will not be present.

The compounds of formula I of this invention contain a chiral center at C5 of the isoxazoline ring, and as such there exist two enantiomers or a racemic mixture of both. This invention relates to both the enantiomers, as well as mixtures containing both the isomers. In addition, depending on substituents, additional chiral centers and other isomeric forms may be present in any of A or $R_1$ group, and this invention embraces all possible stereoisomers and geometric forms in these groups.

The compounds below are typical isoxazolines of this invention. It will be understood that the named compounds do not limit the scope of the invention, but are named merely to help one skilled in the art to understand the invention.

1. (±)-N-[[4,5-Dihydro-3-[4-(4-methoxy-5-oxo-1,3,6-cycloheptatrien-1-yl)phenyl]-5-isoxazolyl]methyl]acetamide;
2. tert-Butyl 4-[4-[5-[(acetylamino)methyl]-4,5-dihydro-3-isoxazolyl]phenyl]-3,6-dihydro-1(2H)-pyridinecarboxylate;
3. (±)-N-[[4,5-Dihydro-3-[3-fluoro-4-(4-methoxy-5-oxo-1,3,6-cycloheptatrien-1-yl)phenyl]-5-isoxazolyl]methyl]acetamide;
4. (±)-N-[[4,5-Dihydro-3-[3,5-difluoro-4-(4-methoxy-5-oxo-1,3,6-cycloheptatrien-1-yl)phenyl]-5-isoxazolyl]methyl]acetamide;
5. (±)-N-[[4,5-Dihydro-3-[4-[1-(4-oxo-2-triazolinyl)-4-piperidinyl]-3,5-difluorophenyl]-5-isoxazolyl]methyl]acetamide;
6. (±)-N-[[4,5-Dihydro-3-[4-[1-(hydroxyacetyl)-2,3,6,7-tetrahydro-1H-azepin-4-yl]phenyl]-5-isoxazolyl]methyl]acetamide;
7. (±)-N-[[4,5-Dihydro-3-[4-[1-(hydroxyacetyl)-2,3,6,7-tetrahydro-1H-azepin-4-yl]-3-fluorophenyl]-5-isoxazolyl]methyl]acetamide;
8. (±)-N-[[4,5-Dihydro-3-[4-[1-(hydroxyacetyl)-2,3,6,7-tetrahydro-1H-azepin-4-yl]-3,5-difluorophenyl]-5-isoxazolyl]methyl]acetamide;
9. N-[[4,5-Dihydro-3-[4-(1,2,3,6-tetrahydropyridinyl)phenyl]-5-isoxazolyl]methyl]acetamide;
10. (±)-N-[[4,5-Dihydro-3-[4-[1-(hydroxyacetyl)-3,6-dihydro-2H-pyridin-4-yl]-3-fluorophenyl]-5-isoxazolyl]methyl]acetamide;
11. (±)-N-[[4,5-Dihydro-3-[4-[1-(hydroxyacetyl)-3,6-dihydro-2H-pyridin-4-yl]-3,5-difluorophenyl]-5-isoxazolyl]methyl]acetamide;
12. (±)-N-[[4,5-Dihydro-3-[4-[1-(hydroxyacetyl)-4-piperidinyl]phenyl]-5-isoxazolyl]methyl]acetamide;
13. (±)-N-[[4,5-Dihydro-3-[4-[1-(hydroxyacetyl)-4-piperidinyl]-3-fluorophenyl]-5-isoxazolyl]methyl]acetamide;
14. (±)-N-[[4,5-Dihydro-3-[4-[1-(hydroxyacetyl)-4-piperidinyl]-3,5-difluorophenyl]-5-isoxazolyl]methyl]acetamide;
15. (±)-N-[[4,5-Dihydro-3-[4-(tetrahydro-2H-pyran-4-yl)phenyl]-5-isoxazolyl]methyl]acetamide;
16. (±)-N-[[4,5-Dihydro-3-[4-(tetrahydro-2H-pyran-4-yl)-3-fluorophenyl]-5-isoxazolyl]methyl]acetamide;
17. (±)-N-[[4,5-Dihydro-3-[4-(tetrahydro-2H-pyran-4-yl)-3,5-difluorophenyl]-5-isoxazolyl]methyl]acetamide;
18. (±)-N-[[4,5-Dihydro-3-[4-(3,6-dihydro-2H-pyran-4-yl)phenyl]-5-isoxazolyl]methyl]acetamide;
19. (±)-N-[[4,5-Dihydro-3-[4-(3,6-dihydro-2H-pyran-4-yl)-3-fluorophenyl]-5-isoxazolyl]methyl]acetamide;
20. (±)-N-[[4,5-Dihydro-3-[4-(3,6-dihydro-2H-pyran-4-yl)-3,5-difluorophenyl]-5-isoxazolyl]methyl]acetamide;
21. (±)-N-[[4,5-Dihydro-3-[4-(tetrahydro-2H-thiopyran-4-yl)phenyl]-5-isoxazolyl]methyl]acetamide;
22. (±)-N-[[4,5-Dihydro-3-[4-(tetrahydro-2H-thiopyran-4-yl)-3-fluorophenyl]-5-isoxazolyl]methyl]acetamide;
23. (±)-N-[[4,5-Dihydro-3-[4-(tetrahydro-2H-thiopyran-4-yl)-3,5-difluorophenyl]-5-isoxazolyl]methyl]acetamide;
24. (±)-N-[[4,5-Dihydro-3-[4-(3,6-dihydro-2H-thiopyran-4-yl)phenyl]-5-isoxazolyl]methyl]acetamide;
25. (±)-N-[[4,5-Dihydro-3-[4-(3,6-dihydro-2H-thiopyran-4-yl)-3-fluorophenyl]-5-isoxazolyl]methyl]acetamide;
26. (±)-N-[[4,5-Dihydro-3-[4-(3,6-dihydro-2H-thiopyran-4-yl)-3,5-difluorophenyl]-5-isoxazolyl]methyl]acetamide;
27. (±)-N-[[4,5-Dihydro-3-[4-(tetrahydro-2H-thiopyran-4-yl)phenyl]-5-isoxazolyl]methyl]acetamide S-oxide;
28. (±)-N-[[4,5-Dihydro-3-[4-(tetrahydro-2H-thiopyran-4-yl)-3-fluorophenyl]-5-isoxazolyl]methyl]acetamide S-oxide;
29. (±)-N-[[4,5-Dihydro-3-[4-(tetrahydro-2H-thiopyran-4-yl)-3,5-difluorophenyl]-5-isoxazolyl]methyl]acetamide S-oxide;
30. (±)-N-[[4,5-Dihydro-3-[4-(tetrahydro-2H-thiopyran-4-yl)phenyl]-5-isoxazolyl]methyl]acetamide S,S-dioxide;
31. (±)-N-[[4,5-Dihydro-3-[4-(tetrahydro-2H-thiopyran-4-yl)-3-fluorophenyl]-5-isoxazolyl]methyl]acetamide S,S-dioxide;
32. (±)-N-[[4,5-Dihydro-3-[4-(tetrahydro-2H-thiopyran-4-yl)-3,5-difluorophenyl]-5-isoxazolyl]methyl]acetamide S,S-dioxide;
33. (±)-N-[[4,5-Dihydro-3-[4-(3,6-dihydro-2H-thiopyran-4-yl)phenyl]-5-isoxazolyl]methyl]acetamide S-oxide;
34. (±)-N-[[4,5-Dihydro-3-[4-(3,6-dihydro-2H-thiopyran-4-yl)-3-fluorophenyl]-5-isoxazolyl]methyl]acetamide S-oxide;
35. (±)-N-[[4,5-Dihydro-3-[4-(3,6-dihydro-2H-thiopyran-4-yl)-3,5-difluorophenyl]-5-isoxazolyl]methyl]acetamide S-oxide;
36. (±)-N-[[4,5-Dihydro-3-[4-(3,6-dihydro-2H-thiopyran-4-yl)phenyl]-5-isoxazolyl]methyl]acetamide S,S-dioxide;
37. (±)-N-[[4,5-Dihydro-3-[4-(3,6-dihydro-2H-thiopyran-4-yl)-3-fluorophenyl]-5-isoxazolyl]methyl]acetamide S,S-dioxide;
38. (±)-N-[[4,5-Dihydro-3-[4-(3,6-dihydro-2H-thiopyran-4-yl)-3,5-difluorophenyl]-5-isoxazolyl]methyl]acetamide, S,S-dioxide;
39. (±)-N-[[4,5-Dihydro-3-[3-fluoro-4-[1-(carboxymethyl)-3-(3-methyl)azetidinyl]phenyl]-5-isoxazolyl]methyl]acetamide;
40. (±)-N-[[4,5-Dihydro-3-[3-fluoro-4-[1-(formyl)-3-(3-methyl)azetidinyl]phenyl]-5-isoxazolyl]methyl]acetamide;
41. (±)-N-[[4,5-Dihydro-3-[3-fluoro-4-[1-(carboxymethyl)-3-azetidinyl]phenyl]-5-isoxazolyl]methyl]acetamide;
42. (±)-N-[[4,5-Dihydro-3-[3-fluoro-4-[1-(formyl)-3-azetidinyl]phenyl]-5-isoxazolyl]methyl]acetamide;
43. (±)-N-[[4,5-Dihydro-3-[3-fluoro-4-[1-(hydroxyacetyl)-3-pyrrolidinyl]phenyl]-5-isoxazolyl]methyl]acetamide;
44. (±)-N-[[4,5-Dihydro-3-[3-fluoro-4-[1-(formyl)-3-pyrrolidinyl]phenyl]-5-isoxazolyl]methyl]acetamide;
45. (±)-N-[[4,5-Dihydro-3-[4-[1-(5-methyl-1,3,4-thiadiazol-2-yl)-3,6-dihydro-2H-pyridin-4-yl]phenyl]-5-isoxazolyl]methyl]acetamide;

46. (±)-N-[[4,5-Dihydro-3-[4-[1-(5-methyl-1,3,4-thiadiazol-2-yl)-3,6-dihydro-2H-pyridin-4-yl]-3-fluorophenyl]-5-isoxazolyl]methyl]acetamide;

47. (±)-N-[[4,5-Dihydro-3-[4-[1-(5-methyl-1,3,4-thiadiazol-2-yl)-3,6-dihydro-2H-pyridin-4-yl]-3,5-difluorophenyl]-5-isoxazolyl]methyl]acetamide;

48. (±)-N-[[4,5-Dihydro-3-[4-[1-(5-methyl-1,3,4-thiadiazol-2-yl)-4-piperidinyl]phenyl]-5-isoxazolyl]methyl]acetamide;

49. (±)-N-[[4,5-Dihydro-3-[4-[1-(5-methyl-1,3,4-thiadiazol-2-yl)-4-piperidinyl]-3-fluorophenyl]-5-isoxazolyl]methyl]acetamide;

50. (±)-N-[[4,5-Dihydro-3-[4-[1-(5-methyl-1,3,4-thiadiazol-2-yl)-4-piperidinyl]-3,5-difluorophenyl]-5-isoxazolyl]methyl]acetamide;

51. (±)-N-[[4,5-Dihydro-3-[4-[1-(4-oxo-2-thiazolinyl)-3,6-dihydro-2H-pyridin-4-yl]phenyl]-5-isoxazolyl]methyl]acetamide;

52. (±)-N-[[4,5-Dihydro-3-[4-[1-(4-oxo-2-thiazolinyl)-3,6-dihydro-2H-pyridin-4-yl]-3-fluorophenyl]-5-isoxazolyl]methyl]acetamide;

53. (±)-N-[[4,5-Dihydro-3-[4-[1-(4-oxo-2-thiazolinyl)-3,6-dihydro-2H-pyridin-4-yl]-3,5-difluorophenyl]-5-isoxazolyl]methyl]acetamide;

54. (±)-N-[[4,5-Dihydro-3-[4-[1-(4-oxo-2-thiazolinyl)-4-piperidinyl]phenyl]-5-isoxazolyl]methyl]acetamide;

55. (±)-N-[[4,5-Dihydro-3-[4-[1-(4-oxo-2-thiazolinyl)-4-piperidinyl]-3-fluorophenyl]-5-isoxazolyl]methyl]acetamide;

56. N-[[4,5-Dihydro-3-[4-[1,2,3,6-tetrahydro-1-(hydroxyacetyl)-4-pyridinyl]phenyl]-5-isoxazolyl]methyl]acetamide;

57. (R)-N-[[4,5-Dihydro-3-[4-[1,2,3,6-tetrahydro-1-(hydroxyacetyl)-4-pyridinyl]phenyl]-5-isoxazolyl]methyl]acetamide;

58. Methyl 4-[4-[5-[(acetylamino)methyl]-4,5-dihydro-3-isoxazolyl]phenyl]-3,6-dihydro-1(2H)-pyridinecarboxylate;

59. N-[[4,5-Dihydro-3-[4-[1,2,3,6-tetrahydro-1-(acetyl)-4-pyridinyl]phenyl]-5-isoxazolyl]methyl]acetamide; or 60. (R)-N-[[4,5-Dihydro-3-[4-(4-pyridinyl)phenyl]-5-isoxazolyl]methyl]acetamide.

The compounds of this invention can be prepared in accordance to one or more of the processes discussed below.

CHART I

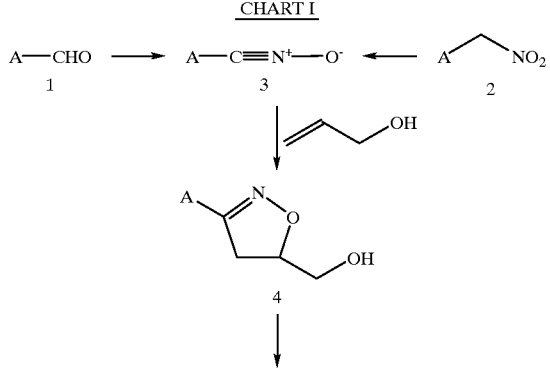

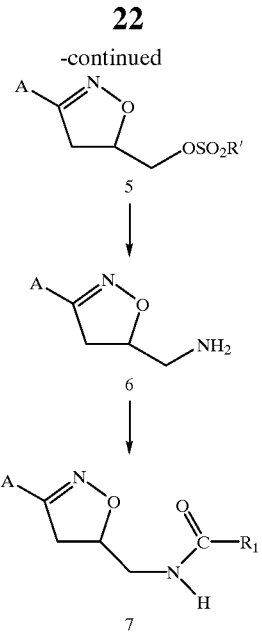

In CHART I, A and $R_1$ are as defined previously. Aryl or heteroaryl aldehyde 1 can be converted to nitrile oxide 3 via three steps: formation of a corresponding oxime, halogenation of resultant oxime to generate an intermediate hydroximinoyl halide, and treatment of this intermediate with a suitable base such as triethylamine to afford nitrile oxide 3. Alternatively, nitrile oxide 3 can be prepared from a aryl or heteroaryl nitromethanes 2. The second method is preferred when functional groups are sensitive to the halogenation step of the first reaction. All these methods are well known to those skilled in the art, and are discussed in further detail in the following references: P. Caramella et al. "1,3-Dipolar Cycloaddition Chemistry", Vol. 1, Chapter 3 of "Nitrile Oxides and Imines", A. Padwa, Ed., John Wiley & Sons, Inc., New York, 1984, pp. 291–392, and references cited therein; C. J. Easton et al., "Advances in Heterocyclic Chemistry", Vol. 60 of "Cycloaddition Reactions of Nitrile Oxides with Alkenes", A. R. Katritzky, Ed., Academic Press, San Diego, 1994, pp. 261–327, and references cited therein; C. Grundmann, et al., *J. Org. Chem.*, 1968, Vol. 33, p. 476; K. C. Liu et al., *J. Org. Chem.* 1980, Vol. 45, p. 3916; T. Mukaiyama et al., *J Am. Chem. Soc.*, 1960, Vol. 82, p. 5339.

The resultant nitrile oxide 3 undergoes a 1,3-dipolar cycloaddition with a allyl alcohol to provide isoxazolines of structure 4. (See the references cited above). Compound 4 is then converted to the corresponding alkylsulfonate or arylsulfonate 5. A representative alkylsulfonyl derivative, the mesylate (R'=CH₃), is prepared by reacting 4 with methanesulfonyl chloride/pyridine or methanesulfonyl chloride/triethylamine/dichloromethane. Utilization of arylsulfonyl chloride reagents, for example p-toluenesulfonyl chloride/pyridine or 3-nitrobenzenesulfonyl chloride/triethylamine/dichloromethane, affords aryl sulfonates such as the tosylate (R'=p-tolyl) or nosylate (R'=3-nitrophenyl), respectively. The alkylsulfonate or arylsulfonate derivative 5 is then converted to the corresponding 5-(aminomethyl)isoxazoline 6 by treatment with aqueous ammonia in a suitable solvent system, for example acetonitrile/isopropanol or tetrahydrofuran/isopropanol, in a sealed reaction vessel, and at a temperature ranging from 40 to 90° C. It will be apparent to those skilled in the art that alternative synthetic procedures for the introduction of the requisite aminomethyl side chain are available. For example, the sulfonate 5 can be reacted with an azide source such as sodium or potassium azide in an aprotic solvent such as N,N-dimethylformamide or 1-methyl-2-pyrrolidinone optionally in the presence of a catalyst such as 18-crown-6 at a temperature of 50 to 90° C. to generate the corresponding 5-(azidomethyl)isoxazoline. The azide moiety is then reduced by hydrogenation with a palladium or platinum catalyst in a suitable solvent such as ethyl acetate or methanol to give structure 6. Alternatively, the azidomethyl intermediate an be reduced to the corresponding amine 6 by a two-step process involving treatment with a trivalent phosphorus compound such as triphenylphosphine in a suitable solvent such as tetrahydrofuran followed by hydrolysis of the resultant iminophosphorane with water. See: M. Vaultier, et al., *Tetrahedron Lett.* 1983, Vol. 24, p. 763. The amine 6 is then acylated by reactions known to those skilled in the art to give isoxazolines of structure 7. For example, the amine 6 can be reacted with an acid chloride or anhydride in a basic solvent system such as pyridine at a temperature ranging from –30 to 30° C. to provide the acylated compound 7. Various methods for acylation reaction are discussed further in J. March, "Advanced Organic Chemistry", 3rd ed., John Wiley & Sons, Inc., New York, 1985, pp. 370–375.

CHART II depicts a method especially adapted to the preparation of the compounds of formula I wherein the A moiety is a phenyl ring with an appended moiety Q or substituted alkene.

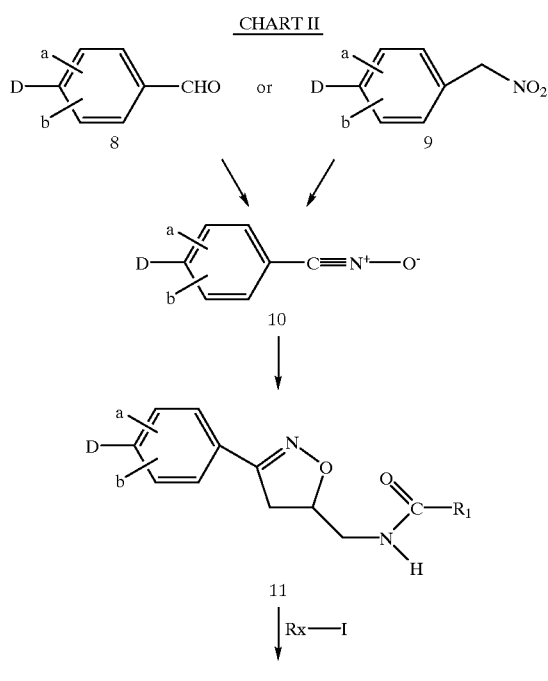

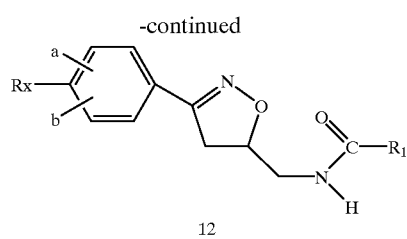

As shown in CHART II, benzaldehyde 8 or phenylnitromethane 9 is converted to compound 11 via the intermediate, nitrile oxide 10. In CHART II, D is bromo, iodo or triflate, the substituent a is $R_{23}$ or $R_{43}$ as defined previously, and the substituent b is hydrogen or $R_{24}$ as defined previously. The process is conducted following the similar procedure described in CHART I. Compound 11 is then reacted with Rx-I (wherein I is an appropriate group such as $SnMe_3$, $SnBu_3$, $B(OH)_2$, or $ZnCl$, and Rx is a Q moiety or a substituted alkene) in the presence of a suitable palladium catalyst such as tetrakis(triphenylphosphine) palladium, bis(triphenylphosphine)palladium dichloride, tris (dibenzylideneacetone)dipalladium and the like in a suitable solvent such as 1,4-dioxane or 1-methyl-2-pyrrolidinone optionally in the presence of tri(2-furyl)phosphine, triphenylarsine, or tri(o-tolyl)phosphine and the like at a temperature in a range from 70° C. to about 100° C. The reaction affords the coupled product 12. This palladium-catalyzed coupling method is discussed in such reference as J. K. Stille, *Angew. Chem., Int. Ed. Engl.,* 1986, Vol. 25, p. 508; S. Hyuga et al., *Chem. Letters,* 1988, p. 809; M. Ogima, et al., *Chem Letters,* 1989, p. 1959; A. Suzuki, *Pure Appl. Chem.* 1991, Vol. 63, p. 419.

Alternatively, the compound 11 can be converted to the corresponding tin derivative (wherein D is tin radical such as $SnMe_3$ or $SnBu_3$) by procedures described in W. D. Wulff et al., *J. Org. Chem.,* 1986, Vol. 51, p. 277. The resultant stannane is then coupled with Rx-I, following the similar palladium-catalyzed method, to provide 12. In this instance, the group I is bromo, iodo, or triflate.

A method for preparation of enantiomerically enriched isoxazolines of formula I can be prepared according to a procedure outlined in CHART III.

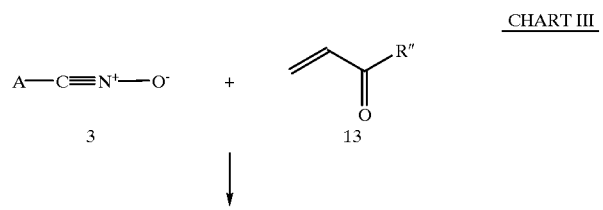

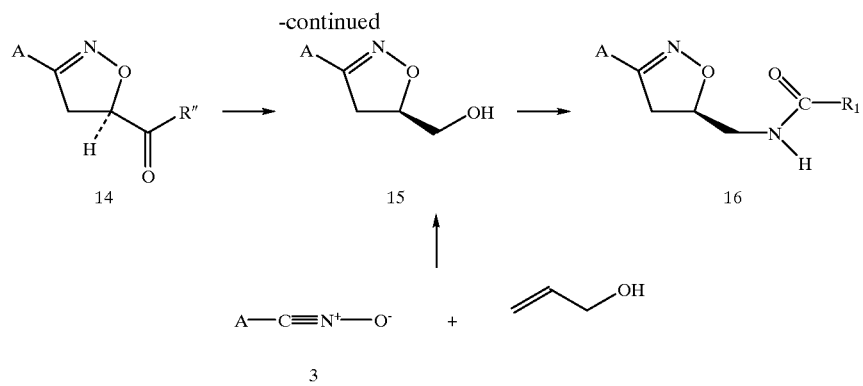

As illustrated in CHART III, reaction of nitrile oxides 3 with α,β-unsaturated esters or amides 13 undergoes an asymmetric 1,3-dipolar cycloaddition to provide compound 14. In this reaction, group R" is a chiral auxiliary used to control the direction of asymmetric induction, and therefore it allows the asymmetric cycloaddition to occur with high steroselectivity. Compound 13 can be prepared from, among the others, Kemp's triacid, Oppolzer's sultam, or chiroinsoitol as described in such references as D. P. Curran et al., *J. Am. Chem. Soc.,* 1989, Vol. 111, p. 9238; J. A. Stack, et al., *Tetrahedron,* 1993, Vol. 49, p. 995; D. P. Curran et al., *Tetrahedron Lett.,* 1988, Vol. 29, p. 3555; W. Oppolzer, et al., *Tetrahedron Lett.,* 1991, Vol. 32, p. 4893; T. Akiyama et al., *Tetrahedron Lett.,* 1992, Vol. 33, p. 5763; Y. H. Kim et al., *Tetrahedron Lett.,* 1993, Vol. 34, p. 6063; C. J. Easton et al., "Advances in Heterocyclic Chemistry", Vol. 60 of "Cycloaddition Reactions of Nitrile Oxides with Alkenes", A. R. Katrikzky, Ed., Academic Press, San Diego, 1994, pp. 261–327, and references cited therein. Use of appropriate chiral auxiliaries to control the steroselectivity of the asymmetric 1,3-dipolar cycloaddition provides access, ultimately, to both enantiomers of 15. For simplicity, only one diastereomer of 14 is presented.

The diastereomeric cycloadducts 14 may be further purified by recrystallization or chromatography. Treatment of the cycloadducts 14 with a suitable reducing agent such as L-selectride (commercially available) in an appropriate solvent such as tetrahydrofuran then provides the enantiomerically enriched 5-(hydroxymethyl)isoxazolines 15. Alternatively, compound 15 can be prepared by treatment of a nitrile oxide 3 with allyl alcohol in the presence of diethylzinc and a (R,R)- or (S,S)-tartaric acid ester, preferably, a diisopropyl ester, in a suitable solvent such as chloroform or dichloromethane and at a temperature in the range of about −20° C. to about 0° C. See Y. Ukaji et al., *Chem. Letters,* 1993, p. 1847. The remaining synthetic steps which lead to compound 16 are similar to the procedures outlined in CHART I.

In addition, racemic esters of structural formula 14 (wherein R" is OMe or OEt) can be resolved by an enzymatic ester hydrolysis procedure described in S. Yang et al., *Monatsh. Chem.,* 1994, Vol, 125, p. 469. Racemic isoxazoline intermediates of structure 11 have also been separated into the individual (R)- and (S)-enantiomers by column chromatography, employing a Chiralpak AD column, and eluting with isopropanol/hexane mixtures as the mobile phase.

As described above, the preparation of the compounds of the invention starts with an appropriately substituted aryl or heteroaryl aldehyde, or with an appropriately substituted aryl or heteroaryl nitromethane. In many instances, the starting aldehydes or nitromethane derivatives are available commercially from chemical firms such as, for example, Aldrich Chemical Company, Inc., Milwaukee, Wis.; TCT America, Portland, Oreg.; Lancaster Synthesis, Windham, N.H.; Maybridge Chemical Col. Ltd., Cornwall, UK—North American agent; Ryan Scientific, Columbia, S.C.; Fluka Chemika, Ronkonkoma, N.Y.; Pfaltz & Bauer, Waterbury, Conn.; and Eastman Organic Chemicals, Eastman Kodak Company, Rochester, N.Y. In any event, all of the starting aldehydes and nitromethane derivatives can be prepared readily by one having ordinary skill in the organic chemistry art utilizing well known procedures. For example, about 40 preparative methods are summarized in R. B. Wagner et al., "Synthetic Organic Chemistry", John Wiley & Sons, Inc., New York, 1953, Chapter 9, pp. 279–315. Furthermore, various methods are discussed in references such as, for example, S. R. Sandler et al., "Organic Functional Group Preparations," 2nd Ed., Academic Press, New York, 1983, Vol. 1, Chapter 7; H. M. Colquhoun et al., "Carbonylation, Direct Synthesis of Carbonyl Compounds", Plenum Press, New York, 1991, Chapter 4; Patai, S., Ed., "The Chemistry of the Carbonyl Group" Interscience Publishers, John Wiley & Sons, Inc., New York, 1966, Chapters 2–7; H. O. House, "Modern Synthetic Reactions", 2nd Ed., W. A. Benjamin, Inc. Menlo Park, Calif. 1972; and H. O. Larson, "Methods of Formation of the Nitro Group in Aliphatic and Alicyclic Systems", Part 1, Chapter of "The Chemistry of the Nitro and Nitroso Groups", Feuer, H., Ed., Interscience Publishers, John Wiley & Sons, Inc., New York, 1969.

The pharmaceutical compositions of this invention may be prepared by combining the compounds of formula I of this invention with a solid or liquid pharmaceutically acceptable carrier, and optionally, with pharmaceutically acceptable adjuvants and excipients employing standard and conventional techniques. Solid form compositions include powders, tablets, dispersible granules, capsules and suppositories. A solid carrier can be at least one substances which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water, water-propylene glycol, and water-polyethylene glycol systems, optionally containing conventional coloring agents, flavoring agents, stabilizers and thickening agents.

The pharmaceutical composition is provided by employing conventional techniques. Preferably the composition is in unit dosage form containing an effective amount of the active component, that is, the compounds of formula I according to this invention.

The quantity of active component, that is, the compounds of formula I according to this invention, in the pharmaceutical composition and unit dosage form thereof may be varied or adjusted widely depending upon the particular application method, the potency of the particular compound and the desired concentration. Generally, the quantity of active component will range between 0.5% to 90% by weight of the composition.

In therapeutic use for treating bacterial infections in humans and other animals that have been diagnosed with bacterial infections, the compounds or pharmaceutical compositions thereof will be administered orally, parenterally and/or topically at a dosage to obtain and maintain a concentration, that is, an amount, or blood-level of active component in the animal undergoing treatment which will be antibacterially effective. Generally, such antibacterially effective amount of dosage of active component will be in the range of about 0.1 to about 100 mg/kg, more preferably about 3.0 to about 50 mg/kg of body weight/day. It is to be understood that the dosages may vary depending upon the requirements of the patient, the severity of the bacterial infection being treated, and the particular compounds being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending of the particular situation. If desired, the daily dose may also be divided into multiple doses for administration, e.g., two to four times per day.

These compounds are useful for the treatment of microbial infections in humans and other warm blooded animals by either parenteral, oral, or topical administration. In general, the preferred form of administration is orally. Pharmaceutical compositions for parenteral administration will generally contain a pharmaceutically acceptable amount of the compounds according to formula I as a soluble salt (acid addition salt or base salt) dissolved in a pharmaceutically acceptable liquid carrier such as, for example, water-for-injection and a suitably buffered isotonic solution having a pH of about 3.5–6. Suitable buffering agents include, for example, trisodium orthophosphate, sodium bicarbonate, sodium citrate, N-methylgucamine, L(+)-lysine and L(+)-arginine, to name a few. The compounds according to formula I generally will be dissolved in the carrier in an amount sufficient to provide a pharmaceutically acceptable injectable concentration in the range of about 1 mg/ml to about 400 mg/ml. The resulting liquid pharmaceutical composition will be administered so as to obtain the above mentioned antibacterially effective amount of sage. The compounds of formula I according to this invention are advantageously administered orally in solid and liquid dosage forms.

The compounds of this invention are useful antimicrobial agents, effective against various human and veterinary pathogens, including multiply-resistant staphylococci and streptococci, as well as anaerobic organisms such as bacteroides and clostridia species, and acid-resistant organisms such as *Mycobacterium tuberculosis* and *Mycobacterium avium*. Humans or animals infected with such pathogens are readily diagnosed by a physician or veterinarian of ordinary skill.

Antimicrobial activity was tested in vitro using the procedure described in National Committee for Clinical Laboratory Standards. Methods for dilution antimicrobial susceptibility tests for bacteria that grow aerobically are disclosed in the third edition of Approved Standard, NCCLS Document M7-A3, Villanova, Pa., 1993. Minimum inhibitory concentration (MIC) values were determined by an agar dilution method (1) in which the test medium was Mueller Hinton agar (MHA; Difco Laboratories, Detroit, Mich.) supplemented with 1% Supplement C (Difco). Serial two-fold dilutions of each compound were prepared using 1.0 ml volumes of sterile distilled water. To each 1.0 ml aliquot was added 9.0 ml of molten agar medium. The drug-supplemented agar was mixed, poured into 15×100 mm petri dishes, and allowed to solidify and dry at room temperature prior to inoculation. The test cultures were grown aerobically overnight at 35° C. on MHA; streptococcal strains were grown on Trypticase Soy Blood Agar Base EH (Difco) supplemented with 5% defibrinated sheep blood (BBL, Bectone Dickinson Company, Cockeysville, Md.). Colonies were harvested with a sterile swab, and cell suspensions were prepared in Trypticase Soy Broth (TSB: Becton Dickinson Company) to equal the turbidity of a 0.5 McFardland standard. A 1:19 dilutation of the suspension was made in TSB; this diluted suspension constituted the inoculum for the assay. The plates containing the drug-supplemented agar were inoculated with a 0.001 ml drop of the cell suspension using a Steers replicator (Melrose Machine Shop, Woodlyn, Pa.), yielding approximately $10^4$–$10^5$ cells per spot. The plates were incubated aerobically at 35° C. for 18 hours and the MIC was read as the lowest concentration of drug that considered to be negative. The data are shown in TABLE 1.

TABLE 1

In Vitro Activity of Compounds Against *Staphylococcus aureus* UC ® No. 9213, *Enterococcus faecalis* UC ® No. 9217 and *Streptococcus Pneumoniae* UC ® No. 9912.

| Example No. | S. a. 9213 (µg/mL) | E. f. 9217 (µg/mL) | S. p. 9912 (µg/mL) |
| --- | --- | --- | --- |
| 1 | 4 | 4 | 1 |
| 4 | 4 | 8 | 2 |
| 5 | 2 | 4 | 0.5 |
| 6 | 16 | 16 | 4 |
| 7 | 8 | 16 | 2 |
| 8 | 1 | 2 | 0.25 |

Antimicrobial activity was also tested in vivo using the Murine Assay procedure. Groups of female mice (six mice weighing 18–20 grams each) were injected intraperitoneally with bacteria which were thawed just prior to use and suspended in brain heart infusion with 4% brewers yeast (*Staphylococcus aureus*). Antibiotic treatment at six dose levels per drug was administered one hour and five hours after infection by either oral intubation or subcutaneous routes. Survival was observed daily for six days. $ED_{50}$ values based on mortality ratios were calculated using probit analysis. The subject compounds were compared against well known antimicrobial U-100592 as controls. U-100592 has been extensively evaluated in this animal model versus vancomycin, and has routinely been shown to be equipotent to vancomycin. See: *Antimicrob. Agents Chemother.*, Vol. 40, No. 6, 1996, pp. 1508–1513; *Antimicrob. Agents Chemother.*, Vol. 40, No. 4, 1996, pp. 839–845; and Upjohn Oxazolidinone Antibacterial Agents, Posters Presented at the 35th Interscience Conference on Antimicrobial Agents and Chemotherapy, San Francisco, 17–20 Sep. 1995, The data are shown in TABLE 2.

TABLE 2

In Vivo Activity of Compounds Against *S. aureus* UC® No. 9213

| Example No. | ED$_{50}$ (μg/mL) | U-100592 ED$_{50}$ (μg/mL) |
|---|---|---|
| 1 | 15.4 | 6.3 |
| 5 | 6.0 | 4.0 |

The compounds, processes and uses of the present invention will be better understood in connection with the following examples, which are intended as an illustration of and not a limitation upon the scope of the invention. Both below and throughout the specification, it is intended that citations to the literature are expressly incorporated by reference herein.

EXAMPLE 1

Preparation of N-[[4,5-Dihydro-3-[4-(4-methoxy-5-oxo-1,3,6-cycloheptatrien-1-yl)phenyl]-5-isoxazolyl]methyl]actamide

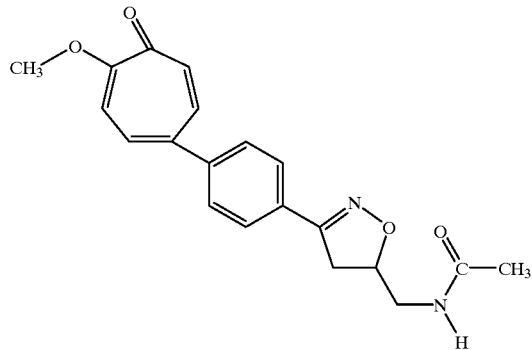

Step 1 Preparation of 4,5-Dihydro-[3-(4-bromophenyl)-5-(hydroxymethyl)]isoxazole To a flask containing 4-bromo-N-hydroxybenzenecarboximidoyl chloride (610 mg. 2.60 mmol) and allyl alcohol (0.14 mL, 2.08 mmol) in methylene chloride (30 mL) at 0° C. under an inert atmosphere is added triethylamine (0.36 mL, 2.60 mmol). The reaction is slowly warmed to ambient temperature, stirred 20 hours, quenched with water (30 mL), and extracted with methylene chloride (2×50 mL). The organic extracts are combined, washed with saline (50 mL), dried over sodium sulfate, concentrated in vacuo and chromatographed on silica gel (230–400 mesh, 200 mL), eluting with chloroform/methanol (99/1). The appropriate fractions are combined (R$_f$=0.06, TLC, hexane/ethyl acetate, 75/25) and concentrated in vacuo to give the title compound, mp 104–105° C.

Step 2 Preparation of N-[[4,5-Dihydro-3-[4-bromophenyl]-5-isoxazolyl]methyl]acetamide To a flame dried flask containing 4,5-dihydro[3-(4-bromophenyl)-5-(hydroxymethyl)]isoxazole (520 mg, 2.03 mmol) in methylene chloride (20 mL) at 0° C. under an inert atmosphere is added triethylamine (0.43 mL, 3.05 mmol) and methanesulfonyl chloride (0.21 mL, 2.13 mmol). The reaction is slowly warmed to ambient temperature, stirred 3 hours, and quenched with water (25 mL). The organic phase is separated, washed with saturated NaHCO$_3$ (25 mL) and saline (25 mL), dried over sodium sulfate and concentrated in vacuo to give crude 4,5-dihydro[3-(4-bromophenyl)-5-[[(methylsulfonyl)oxy]methyl]]isoxazole. The crude 4,5-dihydro[3-(4-bromophenyl)-5-[[(methylsulfonyl)oxy]methyl]]isoxazole (680 mg, 2.03 mmol) is dissolved in tetrahydrofuran (4 mL), isopropanol (4 mL), and concentrated ammonium hydroxide (4 mL) in a thick wall resealable vessel and heated to 100–110° C. for 15 hours. The reaction is cooled to ambient temperature, diluted with ethyl acetate (50 mL), washed with saline (20 mL), dried over sodium sulfate and concentrated in vacuo to give crude 4,5-dihydro[3-(4-bromophenyl)-5-(aminomethyl)]-isoxazole. The crude 4,5-dihydro[3-(4-bromophenyl)-5-(aminomethyl)]isoxazole (520 mg, 2.03 mmol) is dissolved in methylene chloride (15 mL) and cooled to 0° C. under an inert atmosphere. Pyridine (0.51 mL, 6.09 mmol) and acetic anhydride (0.24 mL, 2.54 mmol) are added to the cooled solution and stirred 20 hours at ambient temperature. The reaction is concentrated in vacuo, diluted with methylene chloride (50 mL), washed with saline (25 mL), dried over sodium sulfate, concentrated in vacuo and chromatographed on silica gel (230–400 mesh, 200 mL), eluting with chloroform/methanol (98/2). The appropriate fractions are combined (R$_f$=0.13, TLC, chloroform/methanol, 95/5) and concentrated in vacuo to give the title compound, mp 198–199° C.

Step 3 Preparation of N-[[4,5-Dihydro-3-[4-(4-methoxy-5-oxo-1,3,6-cycloheptatrien-1-yl)phenyl]-5-isoxazolyl]methyl]acetamide To a flame dried flask containing a pre-stirred slurry of 1-methyl-2-pyrrolidinone (5 mL), tris(dibenzylideneacetone)dipalladium (60 mg, 0.07 mmol), tri(2-furyl)phosphone (30 mg, 0.13 mmol) under an inert atmosphere is added N-[[4,5-dihydro-3-[4-bromophenyl]-5-isoxazolyl]methyl]acetamide (193 mg. 0.65 mmol) and 2-methoxy-5-trimethylstannyltropone in 1-methyl-2-pyrrolidinone (5 mL) and heated to 90° C. for 12 hours. The reaction is diluted with ethyl acetate (100 mL) and water (50 mL). The organic phase is separated and the aqueous phase is extracted with methylene chloride (4×50 mL). The organic extracts are combined, dried over sodium sulfate, concentrated in vacuo and chromatographed on silica gel (230–400 mesh, 100 mL), eluting with chloroform/methanol, 95/5). The appropriate fractions are combined (R$_f$=0.10, TLC, chloroform/methanol, 95/5) and concentrated in vacuo to give the title compound, mp >230° C. The compound of Example 1, Step 1, can be prepared enantiomerically pure by a procedure from Ukaji, Y.; Sada, K.; Inomata, K. *Chem. Lett.* 1993, pp 1847–1580.

EXAMPLE 2

Preparation of tert-Butyl 4-[4-[5-[(acetylamino) methyl]-4,5-dihydro-3-isoxazolyl]phenyl]-3,6-dihydro-1(2H)-pyridinecarboxylate

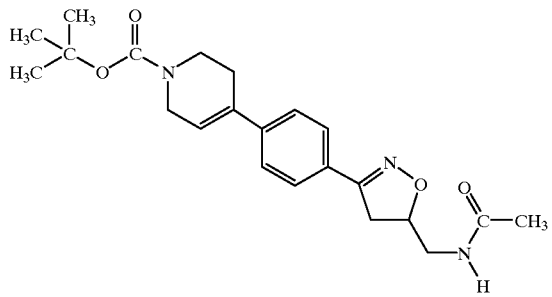

Step 1 Preparation of N-[[4,5-Dihydro-3-[4-(trimethylstanyl)phenyl]-5-isocazolyl]methyl]-acetamide To a flame dried flask containing 1,4-dioxane (10 mL), dichlorobis-(triphenylphosphine)palladium (II) (60 mg, 0.08 mmol) and N-[[4,5-dihydro-3-[4-bromophenyl]-5-isoxazolyl]methyl]acetamide (450 mg., 1.52 mmol) under an inert atmosphere is added hexamethylditin (550 mg, 1.68 mmol) and heated to 100° C. for 12 hours. The reaction is concentrated in vacuo and chromatographed on silica gel (230–400 mesh, 200 mL), eluting with chloroform/acetonitrile (94/6). The appropriate fractions are combined ($R_f$=0.34, TLC, chloroform/methanol, 95/5) and concentrated in vacuo to give the title compound, NMR (CDCL3, 400 MHz) 7.58, 7.52, 6.22, 4.85, 3,59, 3.51, 3.39, 3.12, 1.98, 0.30.

Step 2 Preparation of 3,6-Dihydro-4 [[(trifluoromethyl)sulfonyl]oxy]-1(2H) pyridinecarboxylic acid 1,1-dimethylethyl ester A solution of freshly distilled diisopropylamine (8.70 mL) in dry tetrahydrofuran (133 mL) at −78° C. under $N_2$ is treated with n-butyllithium (1.6M in hexanes, 41.5 mL) dropwise over 10 minutes, and the resulting mixture is stirred at −78° C. for 1 hour and is then treated with a solution of 1-(1,1-dimethylethoxycarbonyl)-4-piperidone (12.0 g) in dry tetrahydrofuran (120 mL) dropwise over 10 minutes. The resulting mixture is stirred at −78° C. for 40 minutes and is then treated with a solution of N-phenyltrifluoromethanesulfonimide (22.0 g) in dry tetrahydrofuran (62 mL) over 5 minutes. The reaction mixture is stirred at −78° C. for 10 minutes and at 0° C. for 4 hours and is then quenched with water (200 mL). The layers are separated, the aqueous phase is extracted with diethyl ether (100 mL) and the combined organic phase is washed with saline (50 mL), dried over anhydrous magnesium sulfate and concentrated under reduced pressure to give the title compound, NMR (CDCl3, 400 MHz) 5.77 4.05, 3.64, 2.45, 1.48.

Step 3 Preparation of tert-Butyl 4-[4-[5-[(acetylamino)methyl]-4,5-dihydro-3-isoxazolyl] phenyl]-3,6-dihydro-1(2H)-pyridinecarboxylate To a flame dried flask containing a pre-stirred slurry of 1-methyl-2-pyrrolidinone (15 mL), tris(dibenzylideneacetone)dipalladium (30 mg, 0.03 mmol), triphenylarsine (4 mg, 0.12 mmol) under an inert atmosphere is added N-[[4,5-dihydro-3-[4-(trimethylstannyl)phenyl]-5-isoxazolyl]methyl]acetamide (580 mg, 1.52 mmol) and 3,6-dihydro-4-[[(trifluoromethyl)sulfonyl]oxy]-1(2H)-pyridinecarboxylic acid 1,1-dimethylethyl ester (450 mg, 1.37 mmol) and stirred for 12 hours. The reaction is diluted with ethyl acetate (100 mL) and water (50 mL). The organic phase is separated, extracted with water (5×50 mL), dried over sodium sulfate, concentrated in vacuo and chromatographed on silica gel (230–400 mesh, 100 mL), eluting with methylene chloride/methanol (99/1). The appropriate fractions are combined ($R_f$=0.28, TLC, chloroform/methanol, 95/5) and concentrated in vacuo to give the title compound, mp 117–120° C.

EXAMPLE 3

Preparation of N-[[4,5-Dihydro-3-[4-(1,2,3,6-tetrahydropyridinyl)phenyl]-5-isoxazolyl]methyl] acetamide

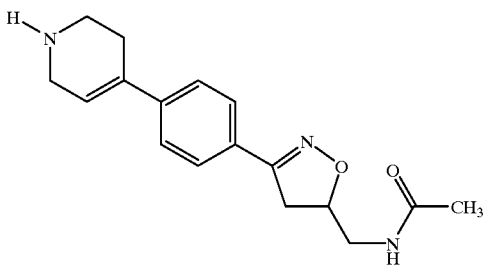

To a flame dried flask containing tert-Butyl 4-[4-[5-[(acetylamino)methyl]-4,5-dihydro-3-isoxyazolyl]phenyl]-3,6-dihydro-1(2H)-pyridinecarboxylate (270 mg, 0.68 mmol) in methylene chloride (15 mL) at 0° C. is added trifluoroacetic acid (1.04 mL, 13.52 mmol). The reaction is stirred 1 hour at 0° C. and 2 hours at ambient temperature. The reaction is poured over a slurry of ice in saturated potassium carbonate (15 mL). The resulting aqueous phase is extracted with methylene chloride (5×25 mL). The extracts are dried over sodium sulfate concentrated in vacuo to give the title compound, MS (ESI+) for $C_{17}H_{21}N_3O_2$ m/z 300.2 $(M+H)^+$.

EXAMPLE 4

Preparation of N-[[4,5-Dihydro-3-[4-[1,2,3,6-tetrahydro-1-(hydroxyacetyl)-4-pyridinyl]phenyl]-5-isoxzoly]methyl]acetamide

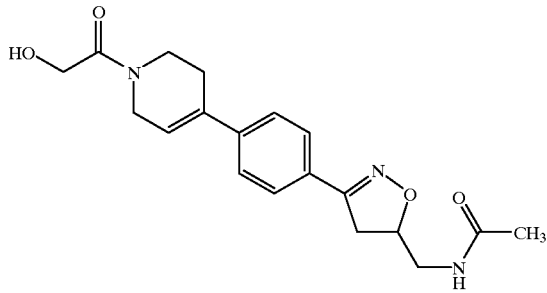

To a flask containing N-[[4,5-dihydro-3-[4-[1,2,3,6-tetrahydropyridinyl]-phenyl]-5-isoxazolyl]methyl]acetamide (185 mg. 0.62 mmol) in methylene chloride (20 mL) and triethylamine (0.17 mL, 1.24 mmol) is added acetoxyacetyl chloride (0.09 mL, 0.81 mmol) at 0° C. under an inert atmosphere. The reaction is warmed to ambient temperature, stirred for 2 hours and concentrated in vacuo. The residue is dissolved in methanol (15 mL) and potassium carbonate (260 mg, 1.88 mmol) is added. The reaction is stirred fifteen hours, concentrated in vacuo, and chromatographed on silica gel (230–400 mesh, 100 mL), eluting with chloroform/methanol (98/2). The appropriate fractions are combined ($R_f$=0.10 TLC, chloroform/methanol, 95/5) and concentrated in vacuo to give the title compound, mp 115–118° C.

EXAMPLE 5

Preparation of (R)-N-[[4,5-Dihydro-3-[4-[1,2,3,6-tetrahydro-1-(hydroxyacetyl)-4-pyridinyl]phenyl]-5-isoxazolyl]methyl]acetamide

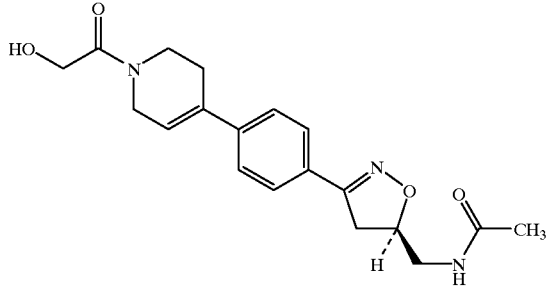

Following the general procedure of EXAMPLE 4 and making noncritical variations but substituting (R)-N-[[4,5-dihydro-3-[4-[1,2,3,6-tetrahydropridinyl]-phenyl]-5-isoxazolyl]methyl]acetamide (280 mg, 0.94 mmol) for N-[[4,5-dihydro-3-[4-[1,2,3,6-tetrahydropyridinyl]phenyl]-5-isoxazolyl]methyl]acetamide the title compound is obtained, HRMS calcd for $C_{19}H_{23}N_3O_4$: 357.1689. Found 357.1694.

EXAMPLE 6

Preparation of Methyl 4-[4-[5-[(acetylamino)methyl]-4,5-dihydro-3-isoxazolyl]phenyl]-3,6-dihydro-1(2H)-pyridinecarboxylate

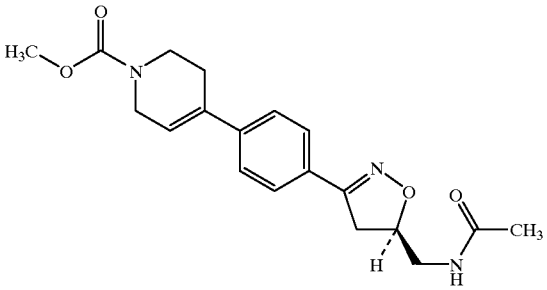

To a flask containing N-[[4,5-dihydro-3-[4-[1,2,3,6-tetrahydropyridinyl]-phenyl]-5-isoxazolyl]methyl] acetamide (300 mg, 1.00 mmol) in acetone (7 mL), water (7 mL) and potassium carbonate (207 mg, 1.50 mmol) is added methylchloroformate (0.09 mL, 1.10 mmol) at 0° C. under an inert atmosphere. The reaction is warmed to ambient temperature stirred fifteen hours, concentrated in vacuo, and chromatographed on silica gel (230–400 mesh, 100 mL), eluting with chloroform/methanol, (98/2). The appropriate fractions are combined ($R_f$=0.14, TLC, chloroform/methanol, 95/5) and concentrated in vacuo to give the title compound, HRMS calcd for $C_{19}H_{23}N_3O_4$: 357.1689. Found: 357.1666.

EXAMPLE 7

Preparation of N-[[4,5-Dihydro-3-[4-[1,2,3,6-tetrahydro-1-(acetyl)-4-pyridinyl]phenyl]-5-isoxazolyl]methyl]acetamide

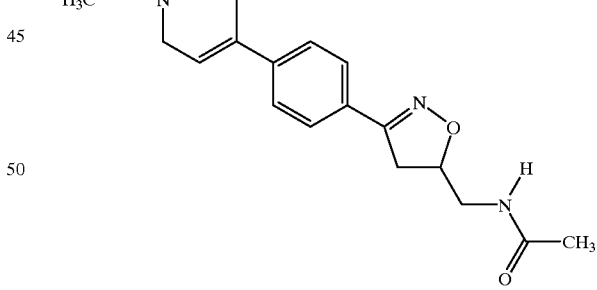

To a flask containing N-[[4,5-dihydro-3-[4-[1,2,3,6-tetrahydropyridinyl]-phenyl]-5-isoxazolyl]methyl] acetamide (300 mg, 1.00 mmol) in methylene chloride (15 mL) and triethylamine (0.28 mL, 2.00 mmol) is added acetyl chloride (0.08 mL, 1.10 mmol) at 0° C. under an inert atmosphere. The reaction is warmed to ambient temperature stirred fifteen hours, concentrated in vacuo, and chromatographed on silica gel (230–400 mesh, 100 mL), eluting with chloroform/methanol (98/2). The appropriate fractions are combined ($R_f$=0.18, TLC, chloroform/methanol, 95/5) and concentrated in vacuo to give the title compound, HRMS calcd for $C_{19}H_{23}N_3O_3$: 341.1739. Found: 341.7125.

EXAMPLE 8

Preparation of (R)-N-[[4,5-Dihydro-3-[4-(4-pyridinyl)phenyl]-5-isoxazolyl]methyl]acetamide

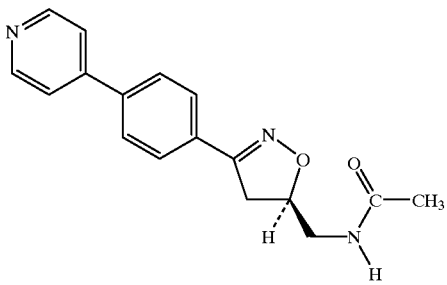

Step 1 Preparation of 4-(Trimethylstannyl)pyridine

To a flame dried flask containing 4-bromopyridine (950 mg, 6.01 mmol), 1,4-dioxane (60 mL) is added hexamethylditin (2.07 g, 6.31 mmol) and dichlorobis-(triphenylphosphine)palladium(II) (110 mg, 0.15 mmol) and heated to 100° C. for 22 hours. The reaction is concentrated in vacuo, and chromatographed on silica gel (230–400 mesh, 100 mL), eluting with chloroform (100) then chloroform/acetonitrile (90/10). The appropriate fractions are combined ($R_f$=0.24, TLC, chloroform/acetonitrile, 90/10) and concentrated in vacuo to give the title compound, MS (ESI+) for $C_8H_{13}NSn$ m/z 244.2 $(M+H)^+$.

Step 2 Preparation of (R)-4,5-Dihydro[3-[4-(4-pyridinyl)phenyl-5-(hydroxymethyl)]]isoxazole To a flame dried flask containing a pre-stirred slurry of 1-methyl-2-pyrrolidinone (8 mL), tri(dibenzylideneacetone) dipalladium (490 mg, 0.54 mmol). tri(2-furyl)phosphine (250 mg, 1.07 mmol) under an inert atmosphere is added (R)-4,5-dihydro[3-(4-bromophenyl)-5-(hydroxymethyl)] isoxazole (1.38 g, 5.37 mmol) and 4-(Trimethylstannyl) pyridine in 1-methyl-2-pyrrolidinone (5 mL) and heated to 90° C. for 12 hours. The reaction is diluted with ethyl acetate (100 mL) and water (50 mL). The organic phase is separated and the aqueous phase is extracted with methylene chloride (4×50 mL). The organic extracts are combined, dried over sodium sulfate, concentrated in vacuo and chromatographed on silica gel (230–400 mesh, 100 mL), eluting with chloroform/methanol (99/1). The appropriate fractions are combined ($R_f$=0.25, TLC, chloroform/methanol, 95/5) and concentrated in vacuo to give the title compound, MS (ESI+) for $C_{15}H_{14}N_2O_2$ m/z 255.1 $(M+H)^+$.

Step 3 Preparation of (R)-N-[[4,5-Dihydro-3-[4-(4-pyridinyl)phenyl]-5-isoxazolyl]methyl]acetamide To a flame drived flask containing (R)-4,5-Dihydro[3-[4-(4-pyrdinyl)phenyl]-5-(hydroxymethyl)]isoxazole (440 mg, 1.73 mmol) in methylene chloride (20 mL) at 0° C. under an inert atmosphere is added triethylamine (0.36 mL, 2.60 mmol) and methanesulfonyl chloride (0.14 mL, 1.82 mmol). The reaction is slowly warmed to ambient temperature, stirred 3 hours, and quenched with water (25 mL). The organic phase is separated, washed with saturated $NaHCO_3$ (25 mL) and saline (25 mL), dried over sodium sulfate and concentrated in vacuo to give crude (R)-4,5-dihydro[3-[4-(4-pyridinyl)phenyl]-5-[[(methylsulfonyl)oxy]methyl] isoxazole. The crude (R)-4,5-dihydro[3-[4-(4-pyridinyl) phenyl]-5-[[(methylsulfonyl)oxy]-methyl]isoxazole (580 mg, 1.73 mmol) is dissolved in tetrahydrofuran (4 mL), isopropanol (4 mL), and concentrated ammonium hydroxide (4 mL) in a thick wall resealable vessel and heated to 100–110° C. for 15 hours. The reaction is cooled to ambient temperature, diluted with ethyl acetate (50 mL), washed with saline (20 mL), dried over sodium sulfate and concentrated in vacuo to give crude (R)-4,5-dihydro[3-[4-(4-pyridinyl)phenyl]-5-(aminomethyl)isoxazole. The crude (R)-4,5-dihydro[3-[4-(4-pyridinyl)phenyl]-5-(aminomethyl)isoxazole (320 mg. 1.57 mmol) is dissolved in methylene chloride (15 mL) and cooled to 0° C. under an inert atmosphere. Pyridine (0.31 mL, 3.78 mmol) and acetic anhydride (0.15 mL, 1.57 mmol) are added to the cooled solution and stirred 20 hours at ambient temperature. The reaction is concentrated in vacuo, diluted with methylene chloride (50 mL), washed with saline (25 mL), dried over sodium sulfate, concentrated in vacuo and chromatographed on silica gel (230–240 mesh, 200 mL), eluting with chloroform/methanol (97/3). The appropriate fractions are combined ($R_f$=0.14, TLC, chloroform/methanol, 95/5) and concentrated in vacuo to give the title compound, mp 244–245° C.

We claim:
1. A compound of the formula I

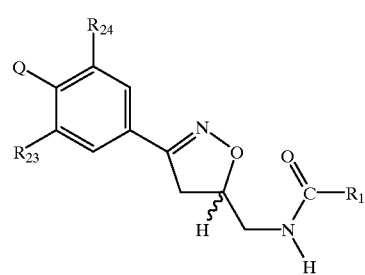

or a pharmaceutical acceptable salt thereof wherein: $R_1$ is
  a) H,
  b) $C_{1-8}$ alkyl optionally substituted with one or more F, Cl, OH, $C_{1-4}$ alkoxy, or acyloxy,
  c) $C_{3-6}$ cycloalkyl, or
  d) $C_{1-8}$ alkoxy
wherein $R_{23}$ and $R_{24}$ are independently
  a) H,
  b) F,
  c) Cl,
  d) $C_{1-2}$ alkyl,
  e) CN,
  f) OH,
  g) $C_{1-2}$ alkoxy,
  h) nitro, or
  i) amino;

Q is

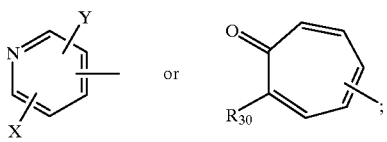 or 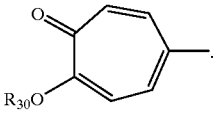;

$R_{30}$ is
a) H,
b) $C_{1-8}$ alkyl optionally substituted with one or more halos, or
c) $C_{1-8}$ alkyl optionally substituted with one or more OH, or $C_{1-6}$ alkoxy;

X is
a) H,
b) F,
c) Cl,
d) Br,
e) $C_{1-8}$alkyl substituted with halo, OH or $C_{3-8}$ cycloalkyl, or
f) $NO_2$.

and Y is
a) H,
b) F,
c) Cl,
d) Br,
e) $C_{1-3}$alkyl,
f) $NO_2$,
g) CN, or
h) $OC_{1-4}$ alkyl.

2. A compound of claim 1 wherein $R_{23}$ and $R_{24}$ are independently H, or F.

3. A compound of claim 1 wherein Q is

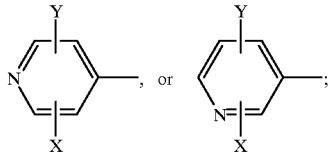

wherein X and Y are the same as claim 1.

4. A compound of claim 3 wherein Y is H X is F, Cl, Br, $C_{1-8}$ alkyl substituted with halo, OH or $C_{3-8}$ cycloalkyl, or $NO_2$.

5. A compound of claim 1 wherein Q is

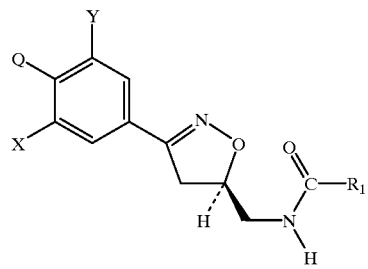

6. A compound of claim 1 or 5 wherein $R_{30}$ is methyl.

7. A compound of claim 1 which is (±)-N-[[4,5-Dihydro-3-[4-(4-methoxy-5-oxo-1,3,6-cycloheptatrien-1-yl)phenyl]-5-isoxazolyl]methyl]acetamide.

8. A compound of the formula I as shown in claim 1 which is formula IA wherein Q, X, Y and $R_1$ are the same as defined in claim 1.

9. A compound of claim 1 wherein $R_1$ is H, methyl, chloromethyl, dichloromethyl, or methoxy.

10. A compound of claim 1 which is a. (±)-N-[[4,5-dihydro-3-[3-fluoro-4-(4-methoxy-5-oxo-1,3,6-cycloheptatrien-1-yl)phenyl]-5-isoxazolyl]methyl]acetamide; or b. (±)-N-[[4,5-dihydro-3-[3,5-difluoro-4-(4-methoxy-5-oxo-1,3,6-cycloheptatrien-1-yl)phenyl]-5-isoxazolyl]methyl]acetamide.

11. A compound of claim 1 which is (R)-N-[[4,5-Dihydro-3-[4-(4-pyridinyl)phenyl]-5-isoxazolyl]methyl]acetamide.

12. A method for treating microbial infections in patients which comprises administering to a patient in need thereof an effective amount of a compound of formula I as shown in claim 1.

* * * * *